United States Patent
Feris et al.

(10) Patent No.: US 10,920,187 B2
(45) Date of Patent: Feb. 16, 2021

(54) ULTRAVIOLET RADIATION PRE-TREATMENT OF WASTEWATER, IMPROVING ITS UTILITY FOR ALGAL CULTIVATION

(71) Applicants: Kevin Feris, Boise, ID (US); Maxine Prior, Meridian, ID (US)

(72) Inventors: Kevin Feris, Boise, ID (US); Maxine Prior, Meridian, ID (US)

(73) Assignee: Boise State University, Boise, ID (US)

( * ) Notice: Subject to any disclaimer, the term of this patent is extended or adjusted under 35 U.S.C. 154(b) by 298 days.

(21) Appl. No.: 14/667,893

(22) Filed: Mar. 25, 2015

(65) Prior Publication Data

US 2015/0275166 A1    Oct. 1, 2015

Related U.S. Application Data

(60) Provisional application No. 61/970,049, filed on Mar. 25, 2014.

(51) Int. Cl.

| | | |
|---|---|---|
| *C12N 1/12* | (2006.01) | |
| *C02F 1/32* | (2006.01) | |
| *C02F 3/32* | (2006.01) | |
| *C12N 13/00* | (2006.01) | |
| *C02F 101/10* | (2006.01) | |
| *C02F 101/16* | (2006.01) | |
| *C02F 103/20* | (2006.01) | |
| *C02F 103/32* | (2006.01) | |
| *C02F 1/28* | (2006.01) | |
| *C02F 1/36* | (2006.01) | |
| *C02F 1/44* | (2006.01) | |
| *C02F 1/00* | (2006.01) | |
| *C02F 103/22* | (2006.01) | |
| *C02F 1/78* | (2006.01) | |

(52) U.S. Cl.
CPC .................. *C12N 1/12* (2013.01); *C02F 1/32* (2013.01); *C02F 3/322* (2013.01); *C12N 13/00* (2013.01); *C02F 1/001* (2013.01); *C02F 1/281* (2013.01); *C02F 1/283* (2013.01); *C02F 1/36* (2013.01); *C02F 1/44* (2013.01); *C02F 1/78* (2013.01); *C02F 2101/105* (2013.01); *C02F 2101/16* (2013.01); *C02F 2103/20* (2013.01); *C02F 2103/22* (2013.01); *C02F 2103/327* (2013.01); *Y02W 10/37* (2015.05)

(58) Field of Classification Search
None
See application file for complete search history.

(56) References Cited

U.S. PATENT DOCUMENTS

| | | |
|---|---|---|
| 2008/0096267 A1 | 4/2008 | Howard et al. |
| 2009/0148927 A1 | 6/2009 | Schroeder et al. |
| 2010/0151558 A1 | 6/2010 | Alianell et al. |
| 2013/0153514 A1* | 6/2013 | Stern .................. C02F 1/325 |
| | | 210/748.1 |

OTHER PUBLICATIONS

Liu et al., Water Research, 46: 3229-3239, 2012.*
Qin et al., Appl Biochem Biotechnol, 172:1121-1130, published online: Oct. 20, 2013.*
Lehtola et al., Water Research, 37:1064-1070, 2003. (Year: 2003).*
Ormeci et al., Journal of Water Supply: Research and Technology, 2005, 54.3: 189-199 (Year: 2005).*
Tamer, E., et al., "Biological treatment of industrial wastes in a photobioreactor", Water Science & Technology, vol. 53, No. 11, (2006), pp. 117-125. Jan. 1, 2006.
Passero, Maxine L., et al, "Ultraviolet radiation pre-treatment modifies dairy wastewater, improving its utility as a medium for algal cultivation", Algal Research, vol. 6, (2014), 13 pages. Sep. 18, 2014.
Cho, Sunja, et al, "Reuse of effluent water from a municpal wastewater treatment plant in microalgae cultivation for biofuel production", Bioresource Technology, vol. 102, (2011), pp. 8639-8645. Apr. 12, 2011.
Santiago, Anibal Fonseca, et al., "Algal biomass production and wastewater treatment in high rate algal ponds receiving disinfected effluent", Environmental Technology, vol. 34, Nos. 13-14, (2013), pp. 1877-1885. May 31, 2013.

\* cited by examiner

*Primary Examiner* — Allison M Fox
*Assistant Examiner* — Qing Xu
(74) *Attorney, Agent, or Firm* — McKee, Voorhees & Sease, PLC

(57) ABSTRACT

The present invention relates to a process of remediating wastewaters, preferably agricultural wastewaters resulting from animal production or contained animal feeding operation sites. The water is treated to promote assimilation of nutrients into algal biomass, which can be harvested and sold, and the resultant wastewater is then purified. According to the invention, short wavelength UV radiation (less than 280 nm wavelength) is used to pretreat wastewater, with the dose determined by absorbance of the water, not by bacterial load. Pretreated water exhibits changes in chromophoric dissolved organic matter that allows for improved and increased algae production by as much as 88%.

16 Claims, 8 Drawing Sheets

ULTRAVIOLET RADIATION PRE-TREATMENT OF WASTEWATER, IMPROVING ITS UTILITY FOR ALGAL CULTIVATION

CROSS-REFERENCE TO RELATED APPLICATIONS

This application claims priority under 35 U.S.C. § 119 to provisional application Ser. No. 61/970,049 filed Mar. 25, 2014, herein incorporated by reference in its entirety.

GRANT REFERENCE CLAUSE

This invention was made with government support under grant numbers FP-91736101-2 and FP-91736101-0 awarded by the Environmental Protection Agency, and grant number DE-AC07-051D14517 awarded by the Department of Energy. The government has certain rights in the invention.

FIELD OF THE INVENTION

The present invention relates to a process of remediating wastewaters such as agricultural production wastewater through assimilation of nutrients into algal biomass; providing opportunity for upcycling into valuable products.

BACKGROUND OF THE INVENTION

Anaerobic digestion (AD) is an energy recovery strategy commonly associated with animal wastes that have a high moisture content where thermochemical conversion is not suitable. AD is one means of organic carbon recovery, producing methane gas ($CH_4$) through bacterial metabolism. The combustion of methane produced by AD simultaneously reduces the GHG footprint of dairies and produces a valuable energy product. The $CH_4$ is generally used to power a suite of generators for onsite electricity generation or to supply base-load electricity to regional electrical grids. A complementary strategy to AD to further reduce GHG emissions from manure management involves bacterial utilization of manure-based organic carbon (sugars, organic acids, lipids) to synthesize polyesters of hydroxyalkanoates known as polyhydroxyalkanoates (PHAs)—a polyester molecule that can be formed into biodegradable plastics. PHA is an intracellular carbon and energy storage molecule produced by bacteria during times of excess carbon and/or nutrient deficiency. Related to algal production, the PHA effluent contains sufficient nutrients and may be conducive to algal biomass production due to better chemical and optical properties, relative to AD effluent. When successive AD and PHA reactor systems are combined for agricultural production waste management, the result is a higher carbon recovery as well as increased conversion into energy and bio-products than when an AD system is implemented alone. However, both processes produce wastewater streams containing significant quantities of mineral nutrients (nitrogen and phosphorus) that require extensive treatment before discharge.

Although attractive and environmentally beneficial, utilizing an agricultural waste stream to promote phototrophic algal growth can be challenging due to the non-ideal growth conditions, resulting in variable growth rates and yield. Yields for algae biomass grown in agricultural wastewaters vary widely, from 6 to 700 mg $L^{-1}$ $day^{-1}$ depending on wastewater source, nutrient content, and dilution levels. Agricultural wastewaters tend to be dark in color, can be nutrient limiting, contain toxic compounds (ammonia and organic acids) and often times have a multitude of competing and predatory organisms (bacteria and protists). The present invention presents a solution to this existing problem. In order to increase biomass yield, some of these limitations can be reduced or eliminated; one method to achieve this is through exposure to ultraviolet radiation (UV).

SUMMARY OF THE INVENTION

The present invention relates to a process of remediating waste waters, preferably agricultural waste waters resulting from animal production, although the invention can include the use and treatment of industrial, municipal, and other wastewater sources containing nitrogen, phosphorus, manure, bacteria and other carbon based by-products). The water is treated to promote assimilation of nutrients into algal biomass, which can be harvested and sold, and the resultant wastewater is then purified. Nutrients and $CO_2$ resulting from oxidation are assimilated by the algae.

According to the invention, short wave radiation UVc (280 nm wavelength or less) is used to pre-treat wastewater. Applicants' have identified a first critical step in treatment of the wastewater that, contrary to prior methods, focuses not just on bacterial load, but primarily on absorbance of the wastewater. According to the invention wastewater with light absorbance levels of 2.4 AU or lower can be effectively treated with UV according to the invention. Applicants have further identified that the essential UV dose includes a critical range that must be higher than about 189 preferably 378.5 $mW-s/cm^2$ up to as high as 500 $mW-s/cm^2$ of UV light will effectively increase algae growth by as much as 88%. According to the invention, it is important to first assess the absorbance of the wastewater which will give vital information about factors conducive to algae production such as presence of light absorbing organic matter, suspended solids, and the like. The UVc dose then optimizes the optical properties of the water to drastically increase algae production and efficiency. The resultant algae and algae by-products may then be provided as input for generating hydrogen gas, bio-fuel, fertilizer, and animal feed additives, and the water is treated as well by removal of nutrient contaminants. By way of example of a commercially viable product, there is increasing interest in bio-diesel as an alternative to petro-diesel and food crop based fuels. There are two problems with the food crop based bio-fuels approach: first, this displaces the food crops grown to feed mankind and second, traditional oilseed crops are neither the most productive nor the most efficient source of vegetable oil. However, microalgae is, by a factor of 8 to 25 for palm oil and a factor of 40 to 120 for rapeseed, the highest potential energy yield temperate vegetable oil crop. Micro-algae are the fastest growing photosynthesizing organisms, and can complete an entire growing cycle every few days. Further, algae does not compete with agriculture for nutrients, requiring neither farmland nor fresh water.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION OF THE PREFERRED EMBODIMENTS

Figure 1A:
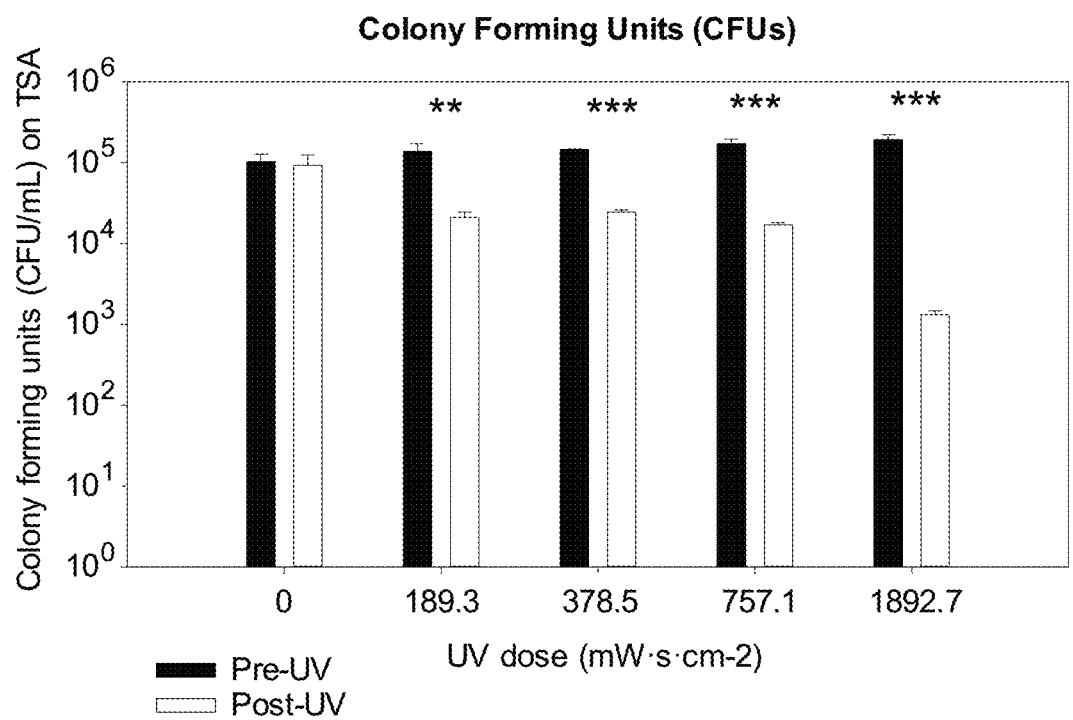
FIG. 1A-D are graphs showing bacterial colony forming units and total dissolved phosphorus as measured for 5% ADE (a) and 5% PHAE (b) before UV treatment (black bars) and after UV treatment (grey bars) for: 0, 189.3, 378.5, 757.1, and 1892.7 mW·s·cm$^{-2}$ UV exposures (means±std. dev). Colony growth on TSA plates is shown here (R2A plates provided similar results). * indicate differences between pre- and post-UV treatment means (n=3; *=P<0.05; =P-value <0.01, *=P-value <0.001
Figure 1B:
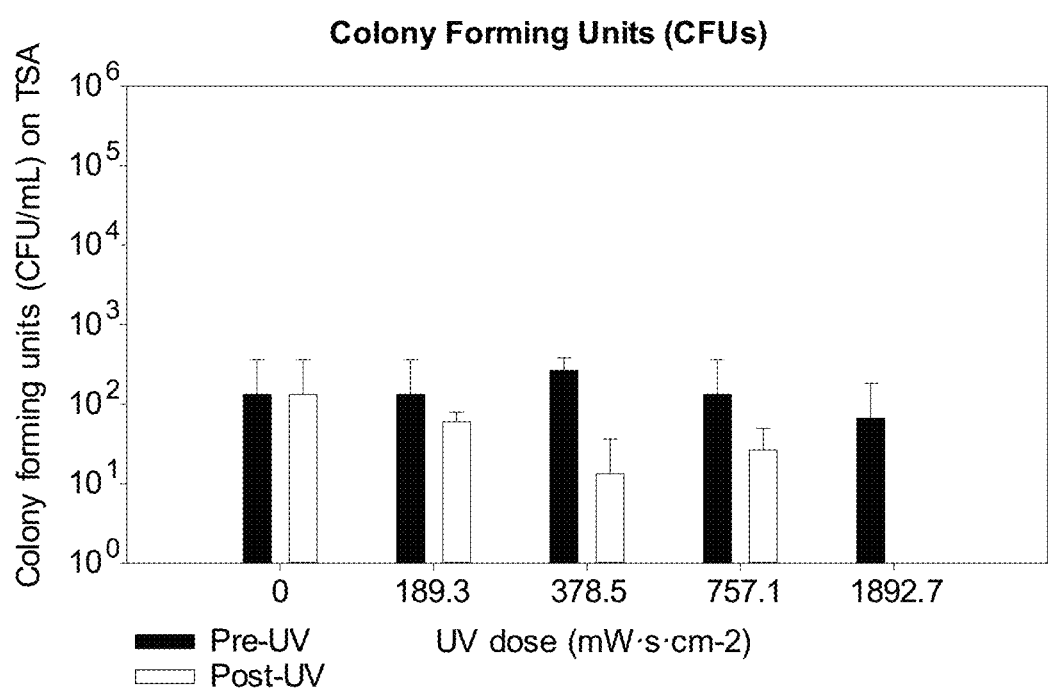
Figure 1C:
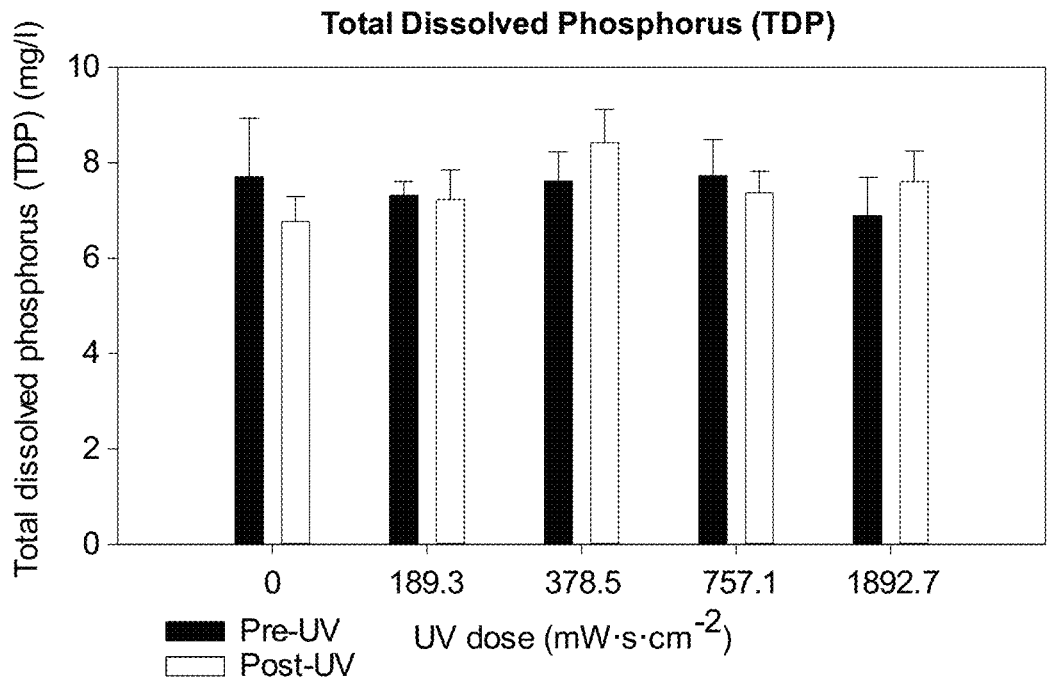
Figure 1D:
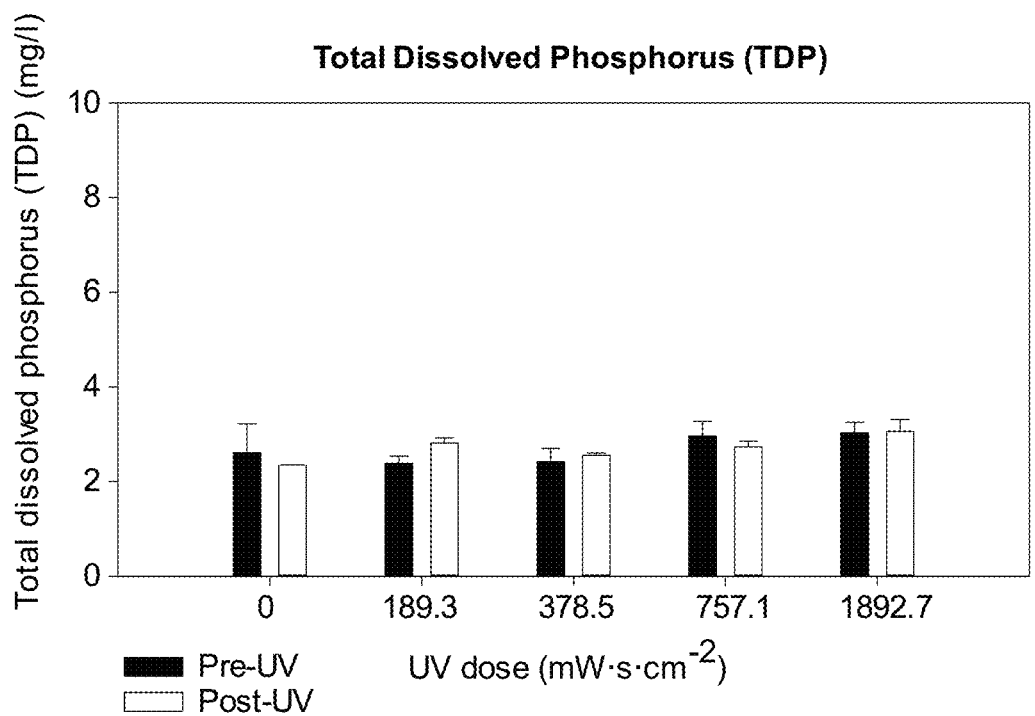

Algae contain lipids, carbohydrates, and protein. Some contain up to 60% lipids, and under some conditions as much as 70% of that amount can be recovered. In other conditions, more than 70% of the lipids present in the algal cell can be recovered. After the lipids are harvested, the oil can be used as a source of, for example, fatty acids, detergent applications, bio-diesel, palm and soy oil alternatives, and the like. Under stress conditions, some algae can produce high grade pigments. These pigments can be isolated during the harvest or processing step and used in areas such as, for example, pharmaceutical encapsulation, medical imaging, food coloring, and the like. The algal bodies can be used as fertilizer, in food products, converted to bio-crude through hydrothermal liquefaction, or directly burned to generate electricity. In some embodiments, the algal bodies can be used to produce cellulosic ethanol.

Algae is of increasing interest in bio-diesel as an alternative to petro-diesel as a source of viable biodiesel that does not displace food crops grown to feed mankind and as traditional oilseed crops are neither the most productive nor the most efficient source of vegetable oil. Microalgae is, the highest potential energy yield temperate vegetable oil crop, by a factor of 8 to 25 for palm oil and a factor of 40 to 120 for rapeseed. Micro-algae are the fastest growing photosynthesizing organisms, and can complete an entire growing cycle every few days. Further, algae does not compete with agriculture for nutrients, requiring neither farmland nor fresh water.

Algae are a diverse group of eukaryotic organisms that contain chlorophyll and carry out photosynthesis. Some contain other photosynthetic pigments which can give the organisms a characteristic color. Algae occur in a wide range of forms from microscopic to macroscopic e.g. seaweeds, some of which are up to 30 meters long. Microscopic algae exist as, for example, single cells e.g. diatoms, in colonies e.g. *Volvox* or in filaments e.g. *Spirogyra*, and the like. Embodiments of the invention utilize algae that can grow photosynthetically utilizing $CO_2$ and sunlight, or heterotrophically using organic carbon sources in addition to a minimum amount of trace nutrients. Various embodiments of the invention can utilize, for example, algae strains such as, *Botryococcus braunii, Chlorella* sp., *Dunaliella tertiolecta, Gracilaria* sp., *Pleurochrysis carterae* (also called CCMP647), *Sargassum* sp., and the like. More particularly, algae strains can include strains with higher oil yields such as *Ankistrodesmus* TR-87: 28-40% dry weight; *Botryococcus braunii*: 29-75% dw; *Chlorella* sp.: 29% dw; *Chlorella protothecoides* (autotrophic/heterotrophic): 15-55% dw; *Cyclotella* DI-35: 42% dw; *Dunaliella tertiolecta*: 36-42% dw; *Hantzschia* DI-160: 66% dw; *Nannochloris*: 31(6-63)% dw; *Nannochloropsis*: 46(31-68)% dw; *Nitzschia* TR-114: 28-50% dw; *Phaeodactylum tricornutum*: 31% dw; *Scenedesmus* TR-84: 45% dw; *Stichococcus*: 33(9-59)% dw; *Tetraselmis suecica*: 15-32% dw; *Thalassiosira pseudonana*: (21-31)% dw; *Crypthecodinium cohnii*: 20% dw; *Neochloris oleoabundans*: 35-54% dw; *Schiochytrium* 50-77% dw.

The present invention relates to a process of remediating wastewaters, preferably agricultural wastewaters resulting from animal production or contained animal feeding operation (CAFO) sites, although the invention can include the use and treatment of industrial, municipal, and other wastewater sources containing nitrogen, phosphorus, trace minerals, bacteria and other carbon based by-products. The wastewater is treated to promote assimilation of nutrients into algal biomass, which can be harvested and sold, and the resultant effluent wastewater is then remediated. Nutrients (nitrogen and phosphorus), carbon, and $CO_2$ are assimilated by the algae.

According to the invention, short wave radiation UVc (280 nm wavelength or less) is used to pre-treat wastewater. Applicants' have identified a first critical step in treatment of the wastewater that, contrary to prior methods, focuses not just on bacterial load, but also on light absorbance of the wastewater. According to the invention wastewater with absorbance levels of 2.4 AU or lower can be effectively treated with UV according to the invention. Applicants have further identified that the essential UV dose includes a critical range that must be higher than about 189 mW-s/cm$^2$ up to as high as 500 mW-s/cm$^2$ of UV light will effectively increase algae formation by as much as 88%.

According to the invention, it is important to first assess the absorbance of the wastewater which will give vital information on factors that determine light transmittance conducive to algae production such as presence of organic matter, suspended solids, and the like. The UVc dose then optimizes the optical properties of the water to drastically increase algae production and efficiency. The resultant algae and algae by-products may then be provided as input for generating hydrogen gas, bio-fuel, fertilizer, and animal feed additives, and the water is treated as well by removal of nutrient contaminants.

Embodiments of the invention include a water supply. The water supply can be recycled from prior uses. The water supply can be treated before use in the system, and such treatments can include, for example, ozone, ultrasound, filtration, hollow fiber filtration, sand filtration, gravel filtration, diatomaceous earth, activated charcoal, and the like. The water supply includes various nutrients.

In certain embodiments of the invention, nutrients are added to the water supply prior to treatment for algae growth. In certain embodiments, added nutrients can include, for example, carbon, nitrates, phosphates manganese, magnesium, potassium, phosphorous, and the like.

In some embodiments, growth medium can be added to the water supply. The appropriate volume of growth medium can be any volume suitable for cultivation of algae biomass production. Suitable growth medium can be any such medium, including, for example, BG-11 growth medium, and the like.

In some embodiments, wastewater being supplied from the wastewater source, can contain additional nutrients, such as nitrogen, phosphates, and/or trace elements (such as iron, zinc), which supplement growth of the algae. In one embodiment, if the wastewater being treated contains sufficient nutrients to sustain the algae growth, it can be possible to use less or no additional growth medium. As the wastewater becomes cleaner due to microorganism uptake of nutrients, growth medium can be added or increased. Factors affecting wastewater input rate include microorganism growth rate, light intensity, culture temperature, initial wastewater nutrient concentrations; and the specific algal uptake rate of certain nutrient(s).

In other embodiments of the invention, wastewater can come from agricultural production such as dairy farms, which can contain high concentrations of ammonia (hundreds to thousands of milligrams per liter of nitrogen as ammonia) and phosphate (tens to hundreds of milligrams per liter of phosphorous as phosphate). Full-strength agricultural wastewater or a lower concentration diluted with water to achieve an acceptable light absorbance (generally 5%) can be used as a "growth medium" for sustaining rapid growth of algae strains In some embodiments of the invention, once the culture has achieved a sufficient degree of growth, the algae can be harvested. Harvest can occur directly from the cultivation raceway or after transfer of the culture to a storage tank. The harvesting steps can include, for example, killing the cells or forcing them into dormancy, separating the cells from the bulk of the media, drying the cells, lysing the cells, separating the desirable components, isolating the desired product, and the like. In some embodiments, not all of these steps are practiced together; various embodiments can combine various different steps and can also include additional steps and/or combinations of various functions into one or several steps. Additionally the steps actually practiced can be practiced in a different order than presented in this list.

Some embodiments of the invention employ a method for harvesting algae which utilizes commercially available equipment such as fixed media filters to remove loosely-adsorbed water to less than 50% weight. Then the retentate (retained by the filter medium) is compressed in a filter press to squeeze out the oil. By way of example, embodiments of the invention can include a raceway having a suitable volume for producing a given biomass yield for a specified hydraulic retention time (HRT).

In certain embodiments, killing or forced dormancy of the cells can be accomplished by a number of means depending on the cells and the product desired. Suitable means include, for example, heating, cooling, the addition of chemical agents such as acid, base, sodium hypochlorite, enzymes, sodium azide, antibiotics, or the like.

In some embodiments of the invention, separation of the cell mass from the bulk of the growth medium can be accomplished in a number of ways. Non-limiting examples include, screening, centrifugation, rotary vacuum filtration, pressure filtration, hydrocycloning, flotation, skimming, sieving, gravity settling, and the like. Other techniques, such as addition of precipitating agents, flocculating agents, or coagulating agents, can also be used in conjunction with these techniques. Flocculating agents can include, for example, iron, phosphatic clay, and the like. In some embodiments, the flocculating agent can be removed with, for example, a hydrocyclone, or the like, and then re-used. In some embodiments, the desired product will be in one of the streams from a separating device and in other cases it will be in the other stream. In some embodiments, two or more stages of separation can be performed. When multiple stages are used, they can be based on the same or a different technique. Non-limiting examples include screening of the bulk of the raceway contents, followed by filtration or centrifugation of the effluent from the first stage.

In some embodiments of the invention, cell lysis can be achieved mechanically or chemically. Non-limiting examples of mechanical methods of lysis include pressure drop devices such as a French press or a pressure drop homogenizer, colloid mills, bead or ball mills, high shear mixers, thermal shock, heat treatment, osmotic shock, sonication, expression, pressing, grinding, expeller pressing and steam explosion. Non-limiting examples of chemical means include the use of enzymes, oxidizing agents, solvents, surfactants, and chelating agents. Depending on the exact nature of the technique being used, the lysis can be done dry, or a solvent such as, for example, water, or the like, or steam can be present. Solvents that can be used for the lysis or to assist in the lysis include, but are not limited to hexane, heptane, supercritical fluids, chlorinated solvents, alcohols, acetone, ethanol, methanol, isopropanol, aldehydes, ketones, chlorinated solvents, fluorinated-chlorinated solvents, and combinations of these. Exemplary surfactants include, but are not limited to, detergents, fatty acids, partial glycerides, phospholipids, lysophospholipids, alcohols, aldehydes, polysorbate compounds, and combinations of these. Exemplary supercritical fluids include, for example, carbon dioxide, ethane, ethylene, propane, propylene, trifluoromethane, chlorotrifluoromethane, ammonia, water, cyclohexane, n-pentane, toluene, and the like. The supercritical fluid solvents can also be modified by the inclusion of water or some other compound to modify the solvent properties of the fluid. Suitable enzymes for chemical lysis include proteases, cellulases, lipases, phospholipases, lysozyme, polysaccharases, and combinations thereof. Suitable chelating agents include, for example, EDTA, porphine, DTPA, NTA, HEDTA, PDTA, EDDHA, glucoheptonate, phosphate ions (variously protonated and non-protonated), and the like. In some cases, combinations of chemical and mechanical methods can be used.

In certain embodiments of the invention, separation of the lysed cells from the product-containing portion or phase can be accomplished by various techniques, for example, centrifugation, hydrocycloning, filtration, flotation, gravity settling, and the like. In some embodiments, it can be desirable to include a solvent or supercritical fluid, for example, to solubilize the desired product, reduce interaction between the product and the broken cells, reduce the amount of product remaining with the broken cells after separation, or to provide a washing step to further reduce losses. Suitable solvents include, for example, hexane, heptane, supercritical fluids, chlorinated solvents, alcohols, acetone, ethanol, methanol, isopropanol, aldehydes, ketones, and fluorinated-chlorinated solvents. Exemplary supercritical fluids include carbon dioxide, ethane, ethylene, propane, propylene, trifluoromethane, chlorotrifluoromethane, ammonia, water, cyclohexane, n-pentane, toluene, and the like, as well as combinations of these. The supercritical fluid solvents can also be modified by the inclusion of water or other compound to modify the solvent properties of the fluid.

In some embodiments of the invention, it will be desirable to dry the cellular material prior to further processing. For example, drying can be desired when the subsequent processing occurs in a remote location or requires larger volumes of material than are provided by a single cultivation batch, or if the material must be campaigned through to achieve more cost-effective processing, or if the presence of water will cause processing difficulties such as emulsion formation, or for other reasons not listed here. Suitable drying systems include, for example, air drying, solar drying, drum drying, spray drying, fluidized bed drying, tray drying, rotary drying, indirect drying, direct drying, and the like.

The pH of the culture can be controlled through the use of a buffer, carbon dioxide, or by addition of an acid or base at the beginning or during the course of the growth cycle. In some cases, both an acid and a base can be used in different zones of the raceway or in the same zone at the same or different times in order to achieve a desirable degree of control over the pH. Non-limiting examples of buffer systems include, for example, carbon dioxide, phosphate, TRIS, TAPS, bicine, tricine, HEPES, TES, MOPS, PIPES, cacodylate, MES, acetate, and the like. Non-limiting examples of acids include, for example, sulfuric acid, hydrochloric acid, lactic acid, acetic acid, and the like. Non-limiting examples of bases include, for example, potassium hydroxide, sodium hydroxide, ammonium hydroxide, ammonia, sodium bicarbonate, calcium hydroxide, sodium carbonate, and the like. Some of these acids and bases, in addition to modifying the pH, can also serve as nutrients for the cells, while carbon dioxide can serve as the carbon source for photosynthesis and carbon storage. The pH of the culture can be controlled to approximate a constant value throughout the entire course of the growth cycle, or it can be changed during the growth cycle. Such changes can be used, for example, to initiate or terminate different metobolic pathways, to force production of one particular product, to force accumulation of a product such as fats, dyes, or bioactive compounds, to suppress growth of other microorganisms, to suppress or encourage foam production, to force the cells into dormancy, to revive them from dormancy, or the like.

In some embodiments of the invention, the pH of the culture can be between 4.0 and 10.0, or between 5.0 and 8.0, or between 6.0 and 7.0. In some embodiments of the invention, the pH can be 6.5.

Likewise, the temperature of the culture can in some embodiments be controlled to approximate a particular value, or it can be changed during the course of the cultivation for the same or different purposes as listed for pH changes. In certain of such embodiments, a temperature control device can be provided that comprises a temperature measurement component that measures a temperature within the system, such as a temperature of the medium, and a control component that can control the temperature in response to the measurement.

Certain embodiments of the system can contain a mechanism for agitating the algae. In some embodiments of the invention, the mechanism for mixing, aeration and/or current flow can be, for example, baffles, mixing foils, air lifts, slotted vented pipes, or the like. The injection of the air results in a mixture of air bubbles and water, which being lighter in weight than water outside the raceway, forces the air/water mixture up. In some embodiments of the invention $CO_2$ will be injected into the air stream also as it can be necessary for growth and reproduction of the algae.

Dairy wastewaters can be remediated through assimilation of nutrients into algal biomass; providing opportunity for upcycling into valuable products. Ultraviolet (UV) radiation can modify aquatic systems, causing changes in dissolved organic matter (DOM), microbial dynamics, nutrient availability and light attenuation. We hypothesized that dairy wastewater would be similarly modified by UV radiation, allowing for better algal growth kinetics.

Two dairy manure wastewaters, anaerobic digester effluent (ADE) and polyhydroxyalkanoate reactor effluent (PHAE) were subjected to UV radiation. A fluence of 1892.7 $mW \cdot s \cdot cm^{-2}$ reduced colony forming units (CFUs) in ADE and PHAE by 99% and 100% respectively, modified fluorescent DOM in both effluents, and reduced light absorbance between 19%-32% for ADE and 7%-22% for PHAE. No measurable changes in dissolved nutrients were detected for either wastewater. These changes resulted in modified growth of *Chlorella vulgaris* as realized by reduced duration and intensity of diphasic lag phase in ADE; growth rate increased linearly with UV fluence and stationary phase was reached 8 to 10 days sooner for all UV doses compared to controls. *Chlorella vulgaris* cultivated in PHAE exposed to UV treatment showed no growth-related response compared to the control.

The dark color in agricultural wastewaters is caused by the presence of dissolved organic matter (DOM) and suspended solids; these limit light penetration through attenuation (absorption and scattering) of light. Chromophoric dissolved organic matter (CDOM) is the optically active fraction of DOM, composed of high molecular weight compounds that absorb light due to conjugated unsaturated bonds. CDOM absorbs light in the blue to ultraviolet wavelength region, similar to the photo reactive pigments chlorophyll b and carotenoids. Light absorbing CDOM effects phototrophic activity to varying degrees depending on algal species and in some cases can stimulate growth by means of reducing the effect of photoinhibition in high light intensity environments. Anaerobically digested dairy manure contains DOM as both volatile solids (VS) and suspended solids (SS) and these quantities can be quite high; 20,900 $mg \cdot L^{-1}$ VS and 23,700 $mg \cdot L^{-1}$ SS for a typical AD digested manure effluent. In order to minimize light attenuation, the CDOM fraction of DOM can be effectively fragmented through UV exposure ($UV_{254}$), depolymerizing high molecular weight chromophores into increasingly smaller molecules and finally resulting in non-light absorbing DOM (non-chromophores) [24]. Additionally, UV exposure partially mineralizes dissolved organic carbon (DOC) to carbon dioxide ($CO_2$), reducing the overall DOC content of the solution [25]. For humic waters that are high in DOM, application of 8 hours of irradiation ($UV_{254}$) causes a 31% reduction in absorbance ($A_{254}$) and a 19% reduction in DOC [25, 26]. Waters obtained from a wild stream show a similar trend when exposed to UV (broad spectrum) for 30 minutes; reducing absorbance ($A_{254}$) and DOC at 49% and 27% respectively.

The invention also relates to methods to track the effect of UV radiation on fluorophores in the wastewaters. As a means to characterize the change in DOM due to UV radiation, the fluorescent component of DOM (fluorophores) can be excited and corresponded emission measured over a range of wavelengths (excitation/emission scan). Fractions of DOM in water and soil are fluorescent in nature and can be characterized by running Ex/Em scans that separate groups of fluorophores based on their Ex/Em pair. A series of Ex/Em scans can be done at increasing excitation wavelengths for a given sample and then plotted together into a contour graph to give an excitation-emission matrix (EEM). The EEM can give information regarding the presence and relative abundance of groups of fluorophores present in a complex mixture based on their respective Ex/Em pair. This method identifies groups of DOM such as humic substances that excite at 230-260 or 320-350 nm and emit at 420-450 nm, or proteins (aromatic acids) that excite at 220 or 275 nm and emit at 300-305 nm (tyrosine-like) and 340-350 nm (tryptophane-like).

UV at high doses ($\geq 204$ mW·s·cm$^{-2}$) has the added effect of oxidizing organically bound phosphorus into more biologically active orthophosphate form. UV radiation (204 mW·s·cm$^{-2}$) of waters containing organic matter (TOC 2.4-2.5 mg·L$^{-1}$) increases microbially active phosphorus (MAP) by 74%-82%. This increase is facilitated through UV assisted reduction of humic iron complexes ($Fe^{3+}$ to $Fe^{2+}$) that bind organic phosphate [28]. The direct stimulation of microbial growth can be attributed to UV radiation of humic waters as a result of degradation of DOM; a linear relationship exists between irradiation time and bacteria growth. Based on this information, UV may be successful at increasing dissolved nutrient concentrations in dairy wastewaters used for algal cultivation.

Agricultural wastewaters tend to be high in bacteria load, the application of UV radiation at 254 nm ($UV_{254}$) can effectively sterilize many microorganisms; decreasing competition and grazing and ultimately facilitating the release of macro and micronutrients associated with the cell lysis. $UV_{254}$ causes inactivation of the microorganism through damage to the nucleic acids (DNA/RNA), inhibiting replication and transcription so that the cell or virus is prevented from multiplying. The efficiency of $UV_{254}$ to sterilize a wastewater is dependent on the state of the organisms present (physiological state, strain diversity, repair mechanisms) as well as factors relating to the state of the wastewater stream (absorption, scattering, reflection). The presence of bacteria colony forming units (CFUs) before and after $UV_{254}$ exposure can be tracked to determine the amount of sterilization imposed on the wastewaters.

The present invention relates to systems and methods for determining the utility of UV radiation to modify dairy wastewater streams, (e.g. anaerobic digester effluent (ADE) and polyhydroxyalkanoate reactor effluent (PHAE) wastewater streams) and methods for quantifying the resulting changes in relation to algal cultivation. These systems and methods will modify multiple parameters in the wastewater streams and ultimately elicit improved algal growth kinetics through biomass yield or growth rate.

To facilitate a better understanding of the present invention, the following examples of preferred or representative embodiments are given. In no way should the following examples be read to limit, or to define, the scope of the invention.

EXAMPLES

Materials and Methods
Dairy Manure Media

The anaerobic digester effluent (ADE) and polyhydroxyalkonoate reactor effluent (PHAE) used for this study were obtained from systems maintained by Dr. Erik R. Coats at the University of Idaho, Department of Civil Engineering. The ADE and the PHAE effluent were centrifuged to remove a majority of solids and stored frozen ($-20°$ C.) in gallon jugs until use. Both effluents were analyzed for nitrogen, phosphorus, and chemical oxygen demand using methods described below. Organic acid composition was provided by Dr. Coats, using a GC/FID method [15].

Algal Cultures

Chlorella vulgaris (UTEX 2714) was acquired from the University of Texas at Austin Culture Collection (UTEX). The C. vulgaris was cultured in triplicate in glass dilution bottles on 4-week intervals using Proteose Medium [33] (per liter of filtered water): 0.25 g $NaNO_3$, 0.025 g $CaCl_2.2H_2O$, 0.075 g $MgSO_4.7H_2O$, 0.075 g $K_2HPO_4$, 0.175 g $KH_2PO_4$, 0.025 g NaCl, 1.0 g Proteose peptone, pH adjusted to 6.8.

Before use, C. vulgaris was rinsed two times with sterile filtered water to remove mineral media according to the following method: a one to two week old volume of culture was centrifuged for 10 minutes at 12,000 rpm, supernatant was poured off and an equal volume of sterile, filtered water was added to rinse the cells. The cells were again centrifuged and supernatant poured off before being reconstituted with a second equal volume of sterile, filtered water. The algal cells were introduced into the ADE or PHAE media using a 5% v/v concentration.

Ultraviolet Radiation Exposure of ADE and PHAE

The UV exposure was done using a Sterilight compact ultraviolet water purification system, model S1Q-PA equipped with a 14 W UV lamp, emitting $UV_{254}$. The UV system was equipped with sterile peristaltic pump tubing at the inlet (bottom) and outlet (top). Before use and between each treatment, the UV system and tubing were thoroughly cleaned with a 10% bleach solution (1000 ml), circulated for 10 minutes from bottom to top of column and through all pump tubing. The bleach was drained and the column and tubing was then rinsed three times with sterile, purified water for 10 minutes each. The rinse water was drained and disposed of each time before new water was added. All open flasks and exposed tubing were kept in a sterile (UV) laminar flow hood in order to reduce contamination.

For each treatment (three replicates), 4000 L of 5% ADE or 5% PHAE solution was prepared using sterile, purified water. A variable speed Watson Marlow peristaltic pump equipped with sterile Bioprene tubing was used to pass the ADE and PHAE solutions through the UV light source using varying flow rates to achieve increasingly higher exposure times and dose rates: 0 sec. UV exposure @ 189 rpm while system was powered down (0 s·cm$^{-2}$), 30 sec. UV exposure @ 189 rpm (189.3 mW·s·cm$^{-2}$), 60 sec. UV exposure @ 94 rpm (378.5 mW·s·cm$^{-2}$), 120 sec. UV exposure @ 47 rpm (757.1 mW·s·cm$^{-2}$), 300 sec. UV exposure @ 19 rpm (1,892.7 mW·s·cm$^{-2}$). UV exposed ADE and PHAE media was collected immediately in sterile glass flasks and stored refrigerated at $4°$ C. until use in algal growth experiments. 10 mL samples from each treatment replicate were frozen at $-20°$ C. for excitation/emission matrix, absorbance scans, and nutrient measurements.

Colony Forming Units (CFUs):

To determine UV sterilization efficiency, samples of the 5% ADE and 5% PHAE from before and after UV exposure were plated on agar plates (TSA and R2A) immediately following the UV exposure. Tryptic Soy Agar (TSA) and Reasoner's 2A agar (R2A) plates were prepared using the following media recipes: TSA (per 1000 mL of purified water): 15 g Tryptone, 5 g Soytone, 5 g Sodium chloride, 15 g Agar. R2A (per 1000 mL of purified water): 0.5 g Proteose peptone, 0.5 g Casamino acids, 0.5 g Yeast extract, 0.5 g Dextrose, 0.5 g soluble starch, 0.3 g Dipotassium phosphate, 0.5 g $MgSO_4.H_2O$, 0.3 g Sodium pyruvate, 15 g Agar, final pH to 7.2±0.2 @ 25° C.

For plating, an aliquot of 100 µL of sample was dispensed on both TSA and R2A plates, spread over the surface of the plate, and incubated for 48 hours at 22° C. Samples were not diluted except for pre-UV and 0 sec UV samples which were diluted at 1:20 (5 µl of sample+95 µl of sterile $DH_2O$). Colony forming units (CFUs) were counted and recorded after 48 hours.

Excitation/Emission Matrix:

Replicate samples from each treatment were pre-filtered using a 0.45 µm syringe filter. Excitation and emission was measured using a Varian Cary Eclipse Fluorescent Spectrophotometer using a slit width of 10, and a step of 10 with excitation range from 200-400 nm and emission range of 350-500 nm (ADE) or 300-500 nm (PHAE). Quartz cuvettes were used for all readings and the machine was zeroed using filtered water. Data was acquired as .csv file in UV-Win software and loaded into EXCEL and SigmaPlot for manipulation. Data from the three treatment replicates was averaged and the change in excitation/emission due to UV treatment was calculated, units were in fluorescence intensity arbitrary units (A.U.). Data was plotted into 3D contour plots using SigmaPlot. The percent change in excitation/emission was calculated by dividing the change in fluorescence intensity by the pre-UV value.

Absorbance Scans:

Replicate treatments were pre-filtered using a 0.45 µm syringe filter. An Aquamate UV/VIS spectrophotometer was used to scan absorbance of samples from 200 nm to 800 nm; the machine was zeroed using purified water. Data was acquired using a LIMS and hyper terminal interface and exported into EXCEL.

Algal Growth Curve Experiments Using UV Treated ADE and PHAE 500 ml increments of each UV treatment (5% ADE or PHAE) were dispensed into 1000 mL Erlenmeyer flasks (three replicates). Each flask was inoculated with a 5% v/v of previously grown and rinsed *Chlorella vulgaris*, fitted with air tubing and an air stone, and a stopper that contained a liquid sampling port, gas introduction port and a gooseneck vent. Each flask was supplied with supplemental 2.5% v/v $CO_2$ in air. The sampling port was equipped with a syringe to draw out daily samples. Compact fluorescent bulbs provided light on a 12-hour light/dark cycle. Flasks were stirred using a stir plate each day before sampling; $OD_{680}$ and chlorophyll were analyzed immediately, cell count was performed either the same day or samples were stored refrigerated until completed. Weekly samples were taken and stored frozen at −20° C. for later nutrient measurements. Biomass concentration was measured at the conclusion of the experiments only.

Determination of Algal Growth and Biomass

These methods were used to track algal biomass production throughout the experiments. Biomass was measured only at the conclusion of each experiment.

Total Chlorophyll Method:

A methanol solvent extraction method was used as adapted from Hipkins [34]. A 0.5 ml sample of each treatment was centrifuged in a tube for 5 minutes at 12,000 rpm to obtain a biomass pellet. The supernatant was removed and disposed of and a 1.0 ml volume of methanol was added to the remaining pellet and sonicated in a bath sonicator for 10 minutes to break up the pellet, lyse algal cells, and solubilize chlorophyll. Samples were then centrifuged for 5 minutes at 12,000 rpm and the supernatant removed and analyzed by spectrophotometry on an Aquamate spectrophotometer via absorbance at 650 nm and 665 nm, zeroed with 100% methanol. Chlorophyll content was determined using the following equations [34]: chlorophyll a=$(16.5*A_{665})-(8.3*A_{650})$, chlorophyll b=$(33.8*A_{650})-(12.5*A_{665})$, total chlorophyll=$(25.8*A_{650})+(4*A_{665})$.

Direct Cell Count:

Algal cell density was measured using a hemocytometer counting chamber. A 10 ul sample volume was inserted into the counting chamber and algal cells were counted at 10× magnification. Depending on the density of each sample, total cell densities were measured by either counting the four 1 mm×1 mm squares on the hemocytometer grid, each with a volume of 0.0001 ml, or by counting five 0.25 mm×0.25 mm squares where each square has a volume of 0.000004 ml, calculating an average cell density and converting to cells/ml.

Absorbance @ 680 nm:

The direct absorbance (optical density) was measured at 680 nm on an Aquamate spectrophotometer, as an indication of turbidity attributed to combined algal cells, bacteria cells, and dissolved organic matter. The machine was zeroed with deionized water. The $OD_{680}$ is highly dependent on dissolved organic matter (digested manure concentration) and therefore used as a relative measurement of algal density.

Direct Biomass:

On the final day of experimental testing, 30 ml of algal suspension was removed from the flask and placed into a pre-weighed drying tin. Samples were dried overnight at 50° C. and 25" Hg vacuum. Dried samples were weighed in the tin and the difference taken as the final dry biomass weight.

Specific Growth Rate Calculation:

The data collected from the direct cell counts was plotted and used to calculate specific growth rate (µ). A best-fit line was drawn using data points corresponding to the growth phase (exponential or lag). The equation for the line was used to calculate cell counts corresponding to the initial and final time points; these points were used in equation 1 to find the specific growth rate for each phase.

$$\mu = \frac{2.303(\log N_t - \log N_o)}{\Delta t} \quad \text{Equation 1}$$

Where:
µ=specific growth rate
No=cell count at initial time point
Nt=cell count at final time point
Δt=time span used for cell count measurement Nutrient Measurements All nutrient measurements were performed via colorimetric methods using a Thermo Aquamate spectrophotometer. Samples were passed through a syringe tip filter (0.45 µm) prior to all nutrient analysis to remove particulates, except for the COD test. Test methods used were: total dissolved nitrogen (Hach persulfate digestion method #10071), ammonia nitrogen ($NH_3$—N) (Hach salicylate method #10023 as adapted from Reardon et al [35]), dissolved nitrate nitrogen ($NO_3^-$—N) (Hach cadmium reduction method #8171), total dissolved phosphorus (Hach PhosVer 3 with acid persulfate digestion method #8190), soluble reactive phosphorus (i.e. orthophosphate) (EPA 365.3), and Chemical oxygen demand (Hach reactor digestion method #8000, USEPA standard method 5220 D). Samples were diluted accordingly in order to obtain the appropriate concentration range for each test; this varied for each experiment and was dependent on the media.

Statistical Analysis

All statistical analysis was performed using raw data and t tests in SigmaPlot 12.3. The levels of significance were: *=P≤0.05, =P≤0.01 and *=P≤0.001.

Example 1

Effect of UV Pre-Treatment Dosing on ADE and PHAE

Solutions of 5% ADE and PHAE were exposed to a series of increasing UV doses (0, 189.3, 378.5, 757.1, and 1892.7 mW·s·cm$^{-2}$) in order to elicit physical and chemical changes that may in turn modify algal growth kinetics. To assess the influence of these treatments on the number of viable bacterial competitors and the physiochemical properties associated with each effluent changes in bacteria colony forming units (CFUs), total dissolved phosphorus (TDP), chromophoric dissolved organic matter (CDOM), and absorbance levels were measured.

Bacterial densities decreased with increasingly higher UV doses for both ADE and PHAE (FIG. 1 A, B) (R2A results were similar, data not shown). There was a 99% and 100% reduction in CFUs for ADE and PHAE respectively using the highest UV fluence (1892.7 mW·s·cm$^{-2}$). All UV doses (≥189.3 mW·s·cm$^{-2}$) provided a statistically significant reduction in CFUs in the ADE and were linearly correlated with the following relationship: [y=−40116 x+1641.3; r$^2$=0.875 where y=UV fluence; x=change in CFUs]. Although bacterial densities in PHAE trended lower after UV exposure the differences were not statistically significant for any of the UV doses, most likely due to the initially low CFU count in the PHAE (averaging over 1000 times lower than in the ADE). UV was successful in providing partial disinfection in both wastewaters. Organic matter in the ADE most likely played a role in diminishing UV effects through shielding (bacteria entrapped within the DOM) and attenuation, although the highest exposure time of 300 seconds achieved a 99% reduction in CFUs. This high retention time (300 seconds) may not be realistic in a larger scale operation and is assumed to be the upper limit for any commercial operation.

There was no measurable change in total dissolved phosphorus (TDP) in samples taken directly before and after UV exposure for all UV exposure levels, in both the ADE and PHAE (FIG. 1 C, D). However, the inability to detect measurable changes in TDP may be due to limitations in our testing procedure that used colorimetric testing (reporting as mg/l) as opposed to microbial activity testing that may be more sensitive, reporting results on a much smaller scale (i.e. µg/l) [27]. Additionally, the UV doses that we utilized (189.3-1892.7 mW·s·cm$^{-2}$) may be nearing and/or at the upper limit where breakdown of DOM causes an increase in TDP concentration. Literature documents the dissolved phosphorus fraction of waters containing DOM typically increase with UV dose up to only 204 mW·s·cm$^{-2}$ with no increase observed at higher UV doses (501 mW·s·cm$^{-2}$) [27]. In our research, the mean TDP showed a slight increase at low UV doses (≤378.5 mW·s·cm$^{-2}$) for both wastewaters, although the means associated with the increase were not statistically significant.

Figure 2:
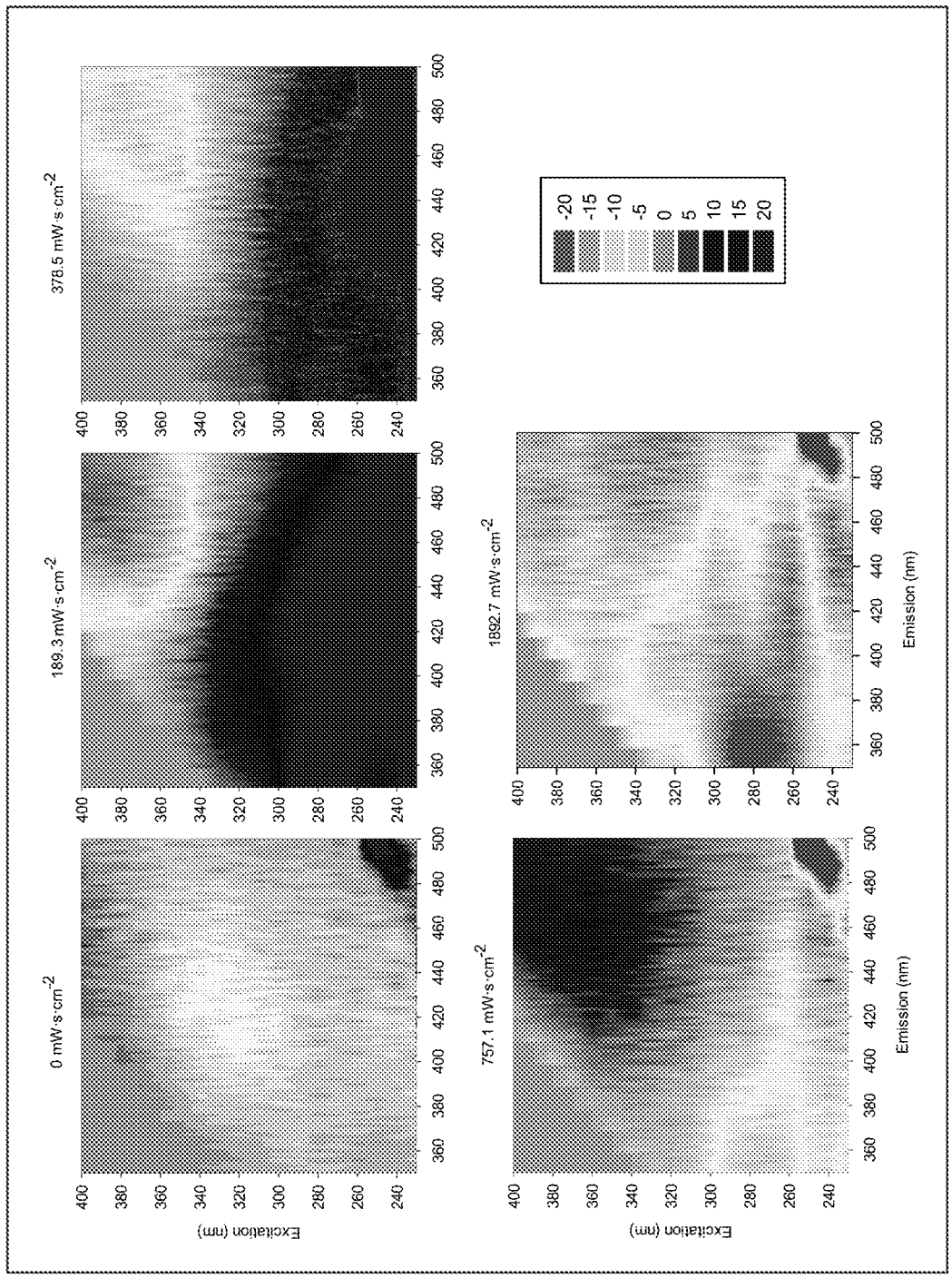
FIG. 2 provides an excitation and emission matrix displaying the change in fluorescence intensity in arbitrary units (A.U.) after $UV_{254}$ radiation in 5% ADE for the following doses (mW·s·cm$^{-2}$): 0, 189.3, 378.5, 757.1, and 1892.7.
Figure 3:
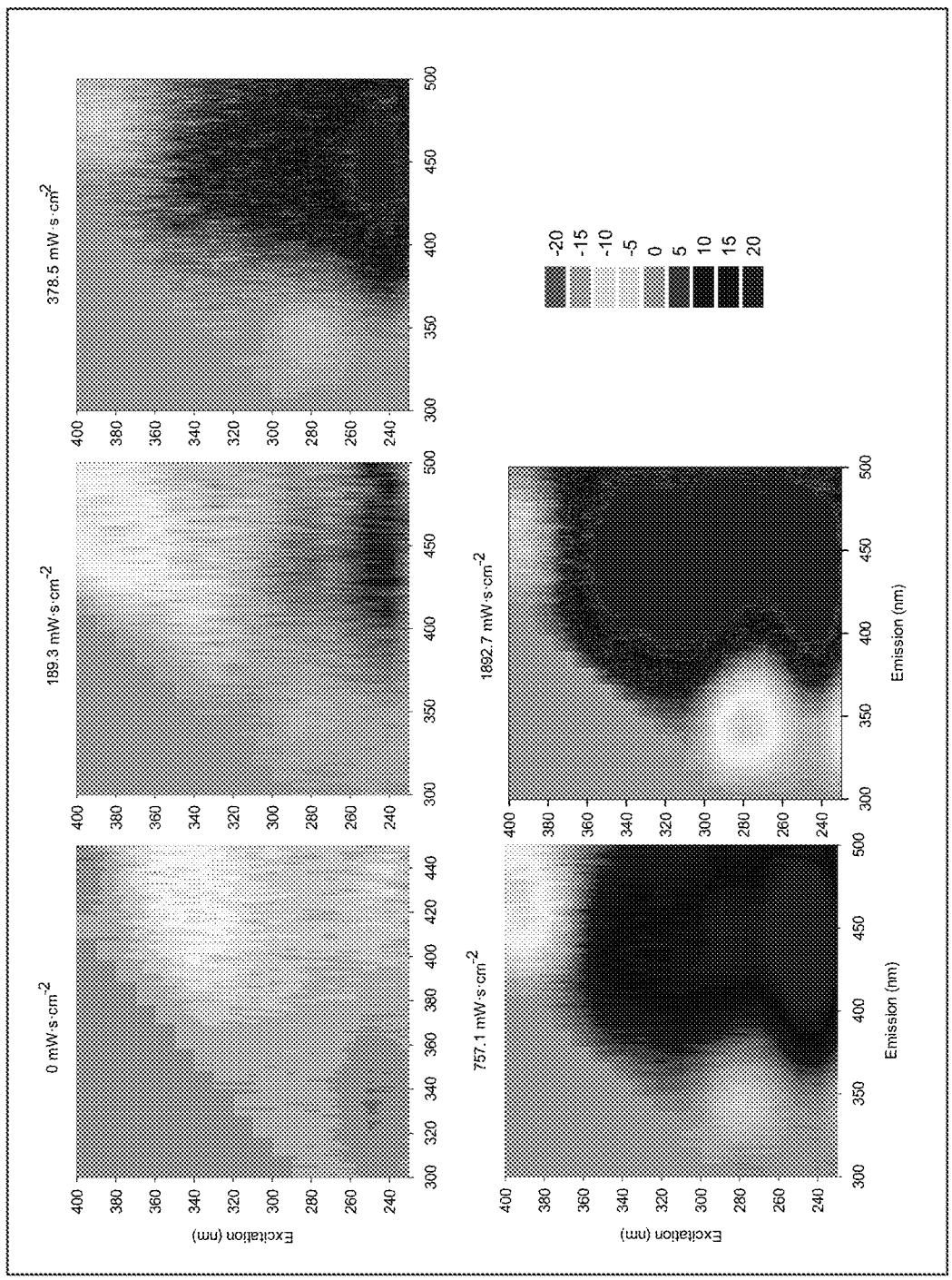
FIG. 3 provides an excitation and emission matrix displaying the change in fluorescence intensity in arbitrary units (A.U.) after $UV_{254}$ radiation in 5% PHA effluent for the following doses (mW·s·cm$^{-2}$): 0, 189.3, 378.5, 757.1, and 1892.7.
Figure 4A:
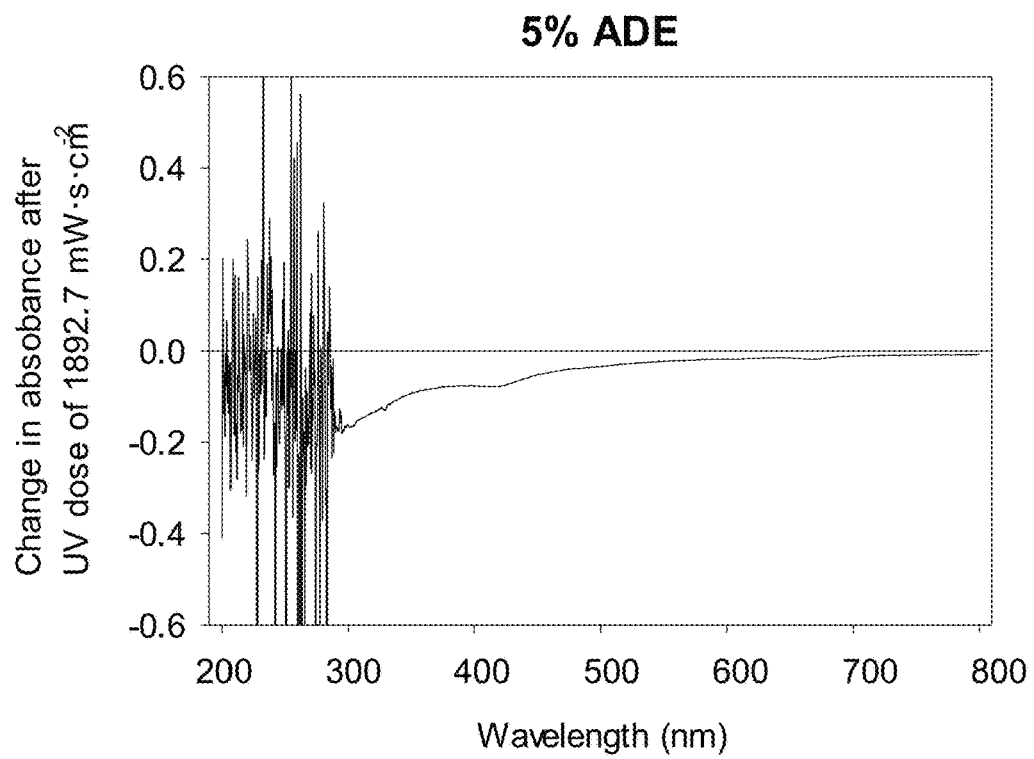
FIGS. 4A-D are graphs showing a change in measured absorbance (absorbance and scattering) after $UV_{254}$ radiation of 5% ADE (a) and (b) and 5% PHAE (c) and (d). Graphs (a) and (c) show the reduction in measured absorbance after the highest dose of 1892.7 mW·s·cm$^{-2}$ over a range of wavelengths (200-800 nm). Graphs (b) and (d) are linear correlations for reduction in absorbance versus UV dose at three absorbance wavelengths (300 nm, 430 nm, and 675 nm).
Figure 4B:
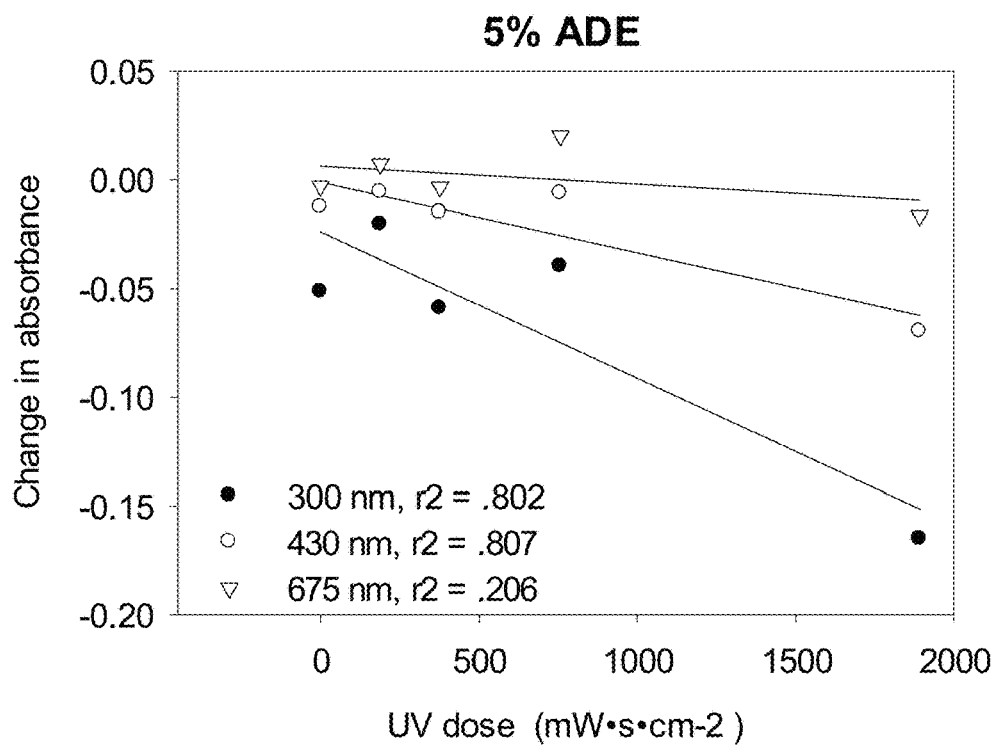
Figure 4C:
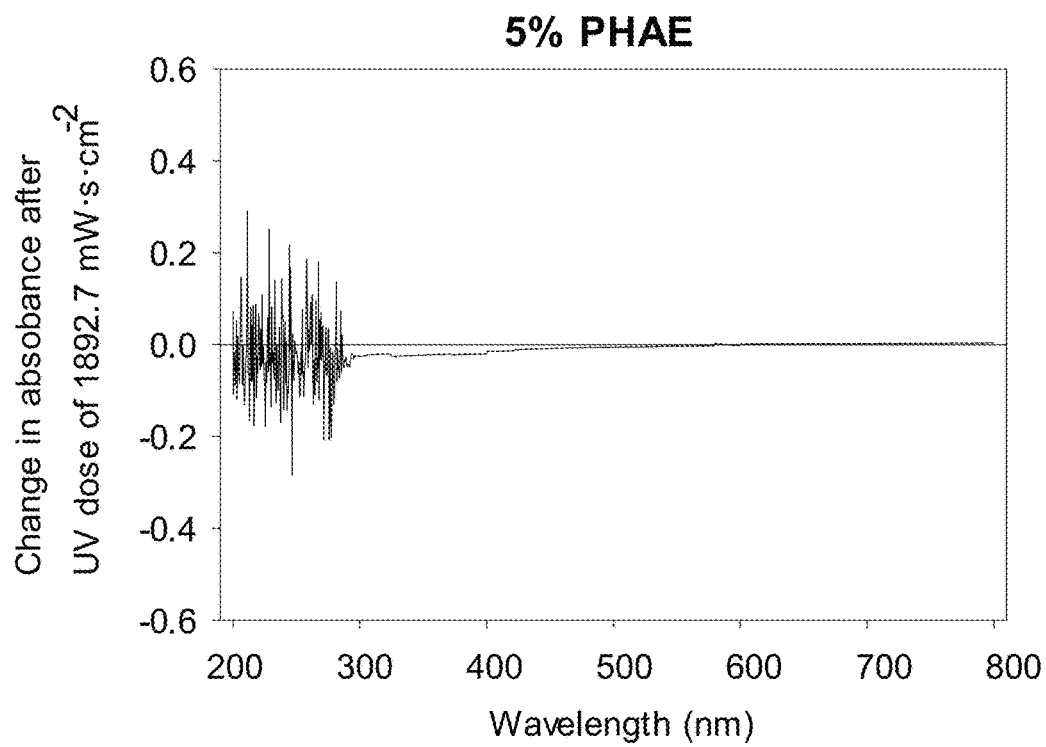
Figure 4D:
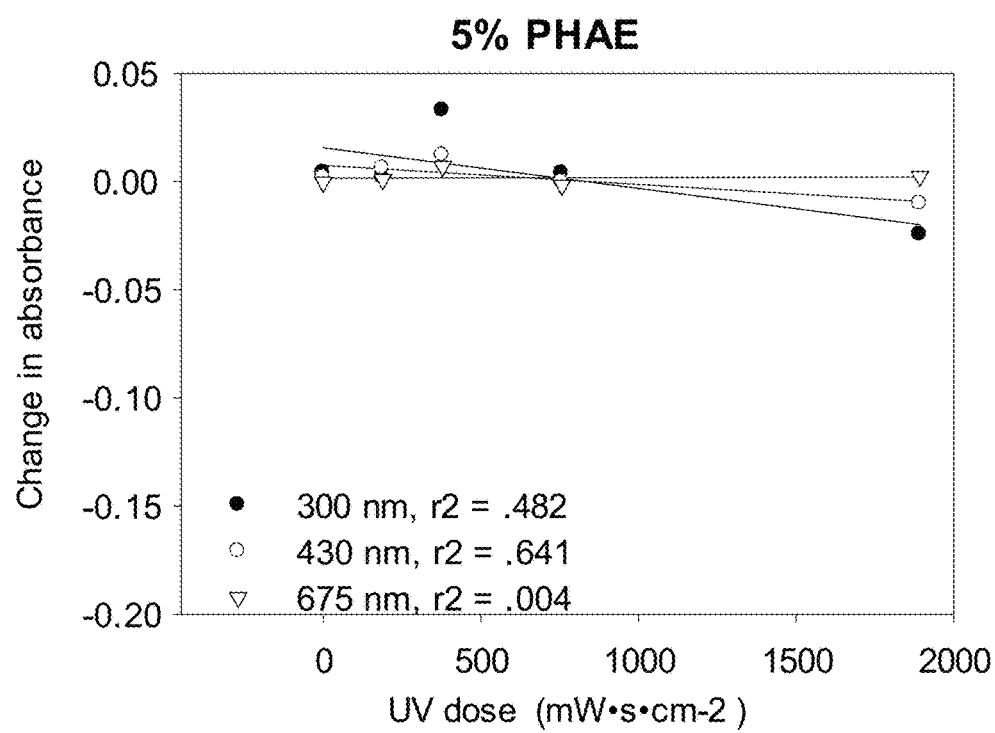

UV exposure altered the composition of the fluorescent CDOM compounds present in both the ADE and PHAE. Excitation/emission (Ex/Em) scans were run for samples taken directly before and after UV exposures as a means to track UV-induced changes in fluorescent CDOM compounds. Data was averaged for each treatment and the change in Ex/Em calculated and plotted on a contour plot to determine relative change in abundance of common fluorescent CDOM groups. Signal intensity is reported in arbitrary units (A.U.) (FIGS. 2, 3). The Ex/Em matrix for both the ADE and PHAE shows a reduction of fluorescence intensity primarily in the area of 280 nm/350-370 nm (Ex/Em) for the highest UV doses. This area is generally associated with fluorescent soluble microbial by-products such as aromatic proteins (i.e., tryptophan) [36]. The highest UV doses of 757.1 and 1892.7 mW·s·cm$^{-2}$ realized a reduction in fluorescence intensity of 7% and 14% in the ADE and 6% and 15% in the PHAE respectively in this area. A similar change in fluorescent intensity is observed for both effluents for the lower UV treatments (189.3 and 378.5 mW·s·cm$^{-2}$) at the 390 nm/480 nm (Ex/Em) pair. This area is generally associated with humic-like compounds that contain aromatic ring structures [36].

The UV dose of 189.3 mW·s·cm$^{-2}$ reduced the fluorescence intensity in the humic-like area by 8% and 5% for ADE and PHAE respectively. Reduction of fluorescence intensity in this area was not as pronounced at the higher UV doses, possibly due to an increased accumulation of low molecular weight (MW) chromophores at this Ex/Em pair. Size exclusion chromatography reveals that UV$_{254}$ has specificity for fragmentation of high MW chromophores in humic matter, resulting in an accumulation of low MW chromophores before eventually depolymerizing into non-chromophores through continued exposure [24].

The reaction follows first-order kinetics and the rate is proportional to the product of the rate of light absorption and its quantum yield [24]. In our case, the higher fluence causes an increase in light absorption and may accelerate breakdown of the high MW chromophores, causing a buildup of lower MW chromophores at the 390/480 nm Ex/Em pair. This could not be confirmed because we did not identify molecular weight fractions in the DOM. However, we can confirm through the Ex/Em matrix that UV$_{254}$ exposure does noticeably modify fluorescent CDOM found in the ADE and PHAE, thereby altering the photoreactive properties of the effluents and potentially influencing light transmission properties that could affect rates of algal production.

Light absorbance of each effluent type was also reduced by the UV treatments. Effluent absorbance was measured over a broad range of wavelengths (200-800 nm) to determine quantitative changes in light absorbance and scattering due to UV$_{254}$ exposure. Replicate samples for each treatment were averaged and the change in absorbance was calculated (FIG. 4 A, C). As a way to track changes in absorbance at wavelengths important to algal cultivation, we looked at the change in measured absorbance at the two absorption maxima for *Chlorella vulgaris* (430 nm and 675 nm). At these wavelengths there was an absorbance reduction of 19% and 32% for ADE, and 7% and 22% for PHAE, respectively. The reduction in absorbance was linearly correlated to UV dose for low wavelengths (including 300 nm and 430 nm), although this correlation decreased with increased wavelength (including 675 nm) (FIG. 4 B, D). Observed changes in absorbance can be directly correlated to a change in the molar concentration of CDOM in solution, according to the Beer-Lambert Law, equation 2.

$$A = \varepsilon l c \quad \text{Equation 2}$$

Where:
A=Absorbance
ε=extinction coefficient
l=path length
c=molar concentration Based on Eq. 2, reductions in the absorbance signal at a given wavelength are directly related to reductions in the molar concentration of the absorbing/scattering species present in the ADE and PHAE. Although we did not identify specific compounds in solution, we can say that the presence of light attenuating compounds in general was reduced by 19% and 32% for ADE and 7% and 22% for PHAE at 430 nm and 675 nm specifically. This reduction is expected to directly translate to increased light penetration and higher growth rates for algal cultivation. For example, the specific algal growth rate is inversely proportional to the initial turbidity (i.e., absorbance and scattering) for algae grown in digested dairy manure [13].

TABLE 1

Organic acid and chemical composition of digested dairy manure and polyhydroxyalkanoate reactor effluent (undiluted).

| | Anaerobically Digested Effluent (ADE) (mg/L) | Polyhydroxyalkonoate Reactor Effluent (PHAE) (mg/L) |
|---|---|---|
| Organic Acids | | |
| Acetate | 456.2 | — |
| Propionate | 155.6 | — |
| Butyrate | 96.5 | — |
| Valerate | 41.1 | — |
| isoValerate | 9.8 | — |
| Caproate | 2.8 | — |
| Chemical Components | | |
| Total dissolved nitrogen (N) | 1226.0 | 499.5 |
| Ammonia ($NH_3$—N) | 760.8 | 59.2 |
| Nitrate ($NO_3$—N) | <10 | 361.2 |
| Total dissolved phosphorus (P) | 96.2 | 33.3 |
| Chemical oxygen demand (COD) | 12,744.4 | 5,575.2 |
| pH | 8.3 | 8.4 |
| Organic Acids | | |
| Acetate | 456.2 | — |
| Propionate | 155.6 | — |
| Butyrate | 96.5 | — |
| Valerate | 41.1 | — |
| isoValerate | 9.8 | — |
| Caproate | 2.8 | — |
| Chemical Components | | |
| Total dissolved nitrogen (N) | 1226.0 | 499.5 |
| Ammonia ($NH_3$—N) | 760.8 | 59.2 |
| Nitrate ($NO_3$—N) | <10 | 361.2 |
| Total dissolved phosphorus (P) | 96.2 | 33.3 |
| Chemical oxygen demand (COD) | 12,744.4 | 5,575.2 |
| pH | 8.3 | 8.4 |

REFERENCES

[1] Bosch, D. J., Wolfe, M. L., Knowlton, K. F., Reducing phosphorus runoff from dairy farms. *Journal of environmental quality* 2006, 35, 918-927.

[2] Ireland. Environmental Protection, A., *Landspreading of organic waste: guidance on groundwater vulnerability assessment of land*, Environmental Protection Agency, Johnstown Castle, Co. Wexford 2004.

[3] Agency, I. E. P., *Landspreading of organic waste: guidance on groundwater vulnerability assessment of land*, Environmental Protection Agency, Johnstown Castle, Co. Wexford 2004.

[4] Liebrand, C. B., Ling, K. C., Research Report 217 2009.

[5] Church, G. A., *Livestock Waste Facilities Handbook*, Midwest Plan Service, Iowa State University, Ames, Iowa 1993.

[6] Phetteplace, H. W., Johnson, D. E., Seidl, A. F., Greenhouse gas emissions from simulated beef and dairy livestock systems in the United States. *Nutrient Cycling in Agroecosystems* 2001, 60, 99-102.

[7] Innovation Center for U.S. Dairy 2011.

[8] Engler, C. R., Jordan, E. R., McFarland, M. J., Lacewell, R. D., Economics and environmental impact of biogas production as a manure management strategy. *Department of Agricultural Engineering*, Texas A&M University 2003.

[9] Weiland, P., Biogas production: current state and perspectives. *Applied microbiology and biotechnology* 2010, 85, 849-860.

[10] Coats, E. R., Loge, F. J., Wolcott, M. P., Englund, K., McDonald, A. G., Synthesis of polyhydroxyalkanoates in municipal wastewater treatment. *Water Environment Research* 2007, 79, 2396-2403.

[11] Liu, H. Y., Hall, P. V., Darby, J. L., Coats, E. R., et al., Production of polyhydroxyalkanoate during treatment of tomato cannery wastewater. *Water Environment Research* 2008, 80, 367-372.

[12] Steinbüchel, A., Perspectives for biotechnological production and utilization of biopolymers: metabolic engineering of polyhydroxyalkanoate biosynthesis pathways as a successful example. *Macromolecular Bioscience* 2001, 1, 1-24.

[13] Wang, L., Li, Y., Chen, P., Min, M., et al., Anaerobic digested dairy manure as a nutrient supplement for cultivation of oil-rich green microalgae *Chlorella* sp. *Bioresource technology* 2010, 101, 2623-2628.

[14] Bosco, F., Chiampo, F., Production of polyhydroxyalcanoates (PHAs) using milk whey and dairy wastewater activated sludge: Production of bioplastics using dairy residues. *Journal of bioscience and bioengineering* 2010, 109, 418-421.

[15] Coats, E. R., Gregg, M., Crawford, R. L., Effect of organic loading and retention time on dairy manure fermentation. *Bioresource technology* 2011, 102, 2572-2577.

[16] Sooknah, R. D., Wilkie, A. C., Nutrient removal by floating aquatic macrophytes cultured in anaerobically digested flushed dairy manure wastewater. *Ecological Engineering* 2004, 22, 27-42.

[17] Kebede-Westhead, E., Pizarro, C., Mulbry, W. W., Production and nutrient removal by periphyton growth under different loading rates of anaerobically digested flushed dairy manure. *Journal of Phycology* 2003, 39, 1275-1282.

[18] Wilkie, A. C., Mulbry, W. W., Recovery of dairy manure nutrients by benthic freshwater algae. *Bioresource technology* 2002, 84, 81-91.

[19] Biller, P., Ross, A., Potential yields and properties of oil from the hydrothermal liquefaction of microalgae with different biochemical content. *Bioresource technology* 2011, 102, 215-225.

[20] Mulbry, W., Westhead, E. K., Pizarro, C., Sikora, L., Recycling of manure nutrients: use of algal biomass from dairy manure treatment as a slow release fertilizer. *Bioresource technology* 2005, 96, 451-458.

[21] Gouveia, L., Oliveira, A. C., Microalgae as a raw material for biofuels production. *Journal of industrial microbiology & biotechnology* 2009, 36, 269-274.

[22] Pittman, J. K., Dean, A. P., Osundeko, O., The potential of sustainable algal biofuel production using wastewater resources. *Bioresource Technology* 2011, 102, 17-25.

[23] Bährs, H., Steinberg, C. E. W., Impact of two different humic substances on selected coccal green algae and cyanobacteria—changes in growth and photosynthetic performance. *Environmental Science and Pollution Research* 2012, 19, 335-346.

[24] Thomson, J., Parkinson, A., Roddick, F. A., Depolymerization of chromophoric natural organic matter. *Environmental science & technology* 2004, 38, 3360-3369.

[25] Corin, N., Backlund, P., Wiklund, T., Bacterial growth in humic waters exposed to UV-radiation and simulated sunlight. *Chemosphere* 1998, 36, 1947-1958.

[26] Gjessing, E. T., Källqvist, T., Algicidal and chemical effect of uv-radiation of water containing humic substances. *Water research* 1991, 25, 491-494.

[27] Lehtola, M. J., Miettinen, I. T., Vartiainen, T., Rantakokko, P., et al., Impact of UV disinfection on microbially available phosphorus, organic carbon, and microbial growth in drinking water. *Water Research* 2003, 37, 1064-1070.

[28] Francko, D. A., Heath, R. T., UV-sensitive complex phosphorus: Association with dissolved humic material and iron in a bog lake. *Limnology and Oceanography* 1982, 564-569.

[29] Christian, G. D., Callis, J. B., Davidson, E. R., Array detectors and excitation-emission matrices in multicomponent analysis. *Modern Fluorescence Spectroscopy* 1981, 4, 111-165.

[30] Coble, P. G., Characterization of marine and terrestrial DOM in seawater using excitation-emission matrix spectroscopy. *Marine Chemistry* 1996, 51, 325-346.

[31] von Sonntag, C., Kolch, A., Gebel, J., Oguma, K., Sommer, R., *Effects and technologies*, Sep. 22-24, 2003, Karlsruhe 2003.

[32] Hijnen, W. A. M., Beerendonk, E. F., Medema, G. J., Inactivation credit of UV radiation for viruses, bacteria and protozoan (oo) cysts in water: a review. *Water Research* 2006, 40, 3-22.

[33] UTEX.

[34] Hipkins, M., *Photosynthesis energy transduction a practical approach*, IRL press, Oxford, Washington D.C. 1986.

[35] Reardon, J., Foreman, J. A., Searcy, R. L., New reactants for the colorimetric determination of ammonia. *Clinica chimica acta; international journal of clinical chemistry* 1966, 14, 203.

[36] Chen, W., Westerhoff, P., Leenheer, J. A., Booksh, K., Fluorescence excitation-emission matrix regional integration to quantify spectra for dissolved organic matter. *Environmental science & technology* 2003, 37, 5701-5710.

[37] Monod, J., The growth of bacterial cultures. *Annual Reviews in Microbiology* 1949, 3, 371-394.

[38] Bolier, G., Donze, M., On the accuracy and interpretation of growth curves of planktonic algae. *Hydrobiologia* 1989, 188, 175-179.

[39] Thornber, C. S., Functional properties of the isomorphic biphasic algal life cycle. *Integrative and comparative biology* 2006, 46, 605-614.

[40] Bettenbrock, K., Fischer, S., Kremling, A., Jahreis, K., et al., A quantitative approach to catabolite repression in *Escherichia coli*. *Journal of Biological Chemistry* 2006, 281, 2578-258

Example 2

Algal Response to UV-Pretreatment of ADE and PHAE

Figure 5A:
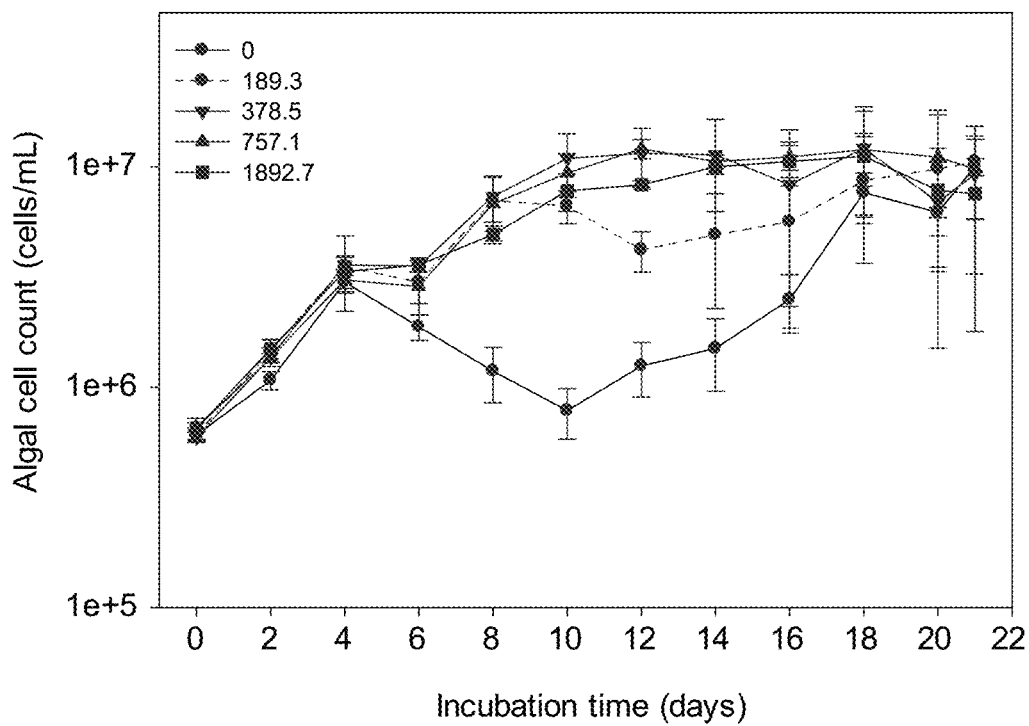
FIGS. 5A-B show growth curves of *Chlorella vulgaris* cultivated in 5% ADE (a) and 5% PHAE (b) after UV pre-treatment at the following doses: 0, 189.3, 378.5, 757.1, and 1892.7 mW·s·cm$^{-2}$. Error bars indicate one standard deviation from the mean, n=3.

The utility of UV radiation to modify ADE and PHAE to better accommodate algal growth was tested through monitoring growth kinetics (growth rate, lag phase, biomass yield). Growth of *C. vulgaris* as measured through a direct cell count was dramatically modified in $UV_{254}$ irradiated ADE while PHAE did not show a measurable response (FIG. 5).

The cultivation of *C. vulgaris* in ADE resulted in a distinct bimodal growth pattern with a primary and secondary exponential phase separated by a lag phase characterized by a negative growth rate, this phenomena was not seen in the PHAE. This phenomenon may be similar to diauxie that was observed by Monod (1949) in bacteria cultures exposed to two carbon substrates. During diauxie, a primary exponential phase is observed during utilization of the most preferred substrate followed by a minimum or negative growth rate (lag phase) and finally a secondary exponential phase associated with the second substrate [37]. The lag phase is thought to be a transition period elicited by the organism to begin production of specific enzymes needed to utilize the secondary substrate [37]. The exact reason for diauxic growth in our research is complicated by the complex undefined wastewater environment, although we can theorize that the algae is forced to make a similar metabolic transition due to either unavailable nutrients, inhibitory components, low light availability, or high bacterial load.

Figure 6A:
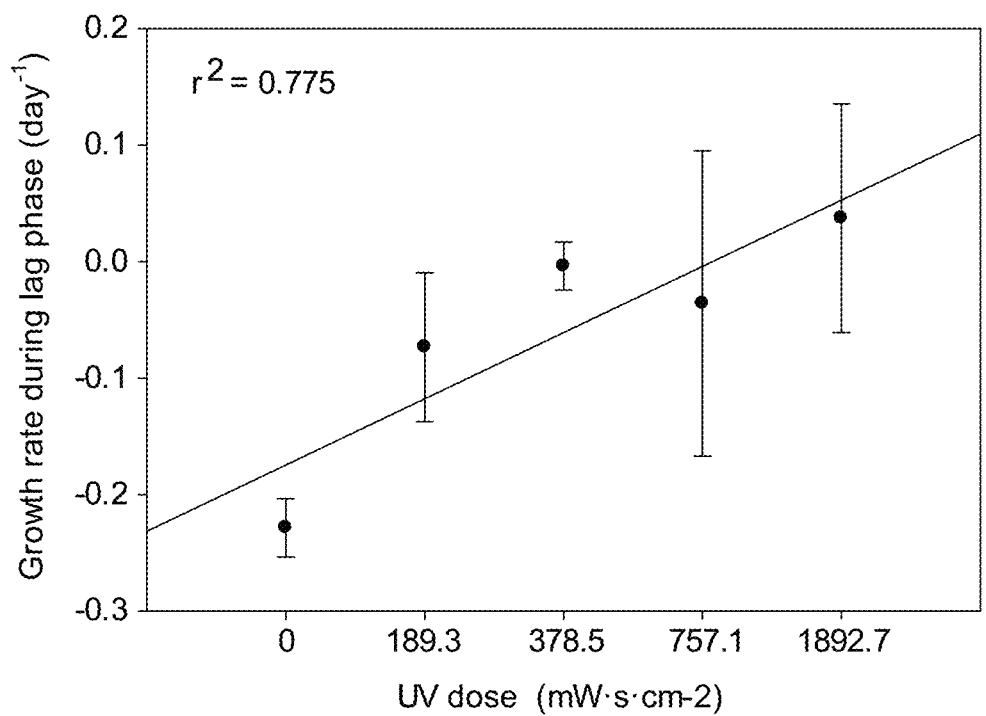
FIGS. 6A-B are graphs showing the linear relationship for lag phase growth rate of *C. vulgaris* cultivated in 5% ADE as a function of UV dosing (a) and bacteria loading rate (b). Error bars indicate one standard deviation from the mean, n=3.
Figure 6B:
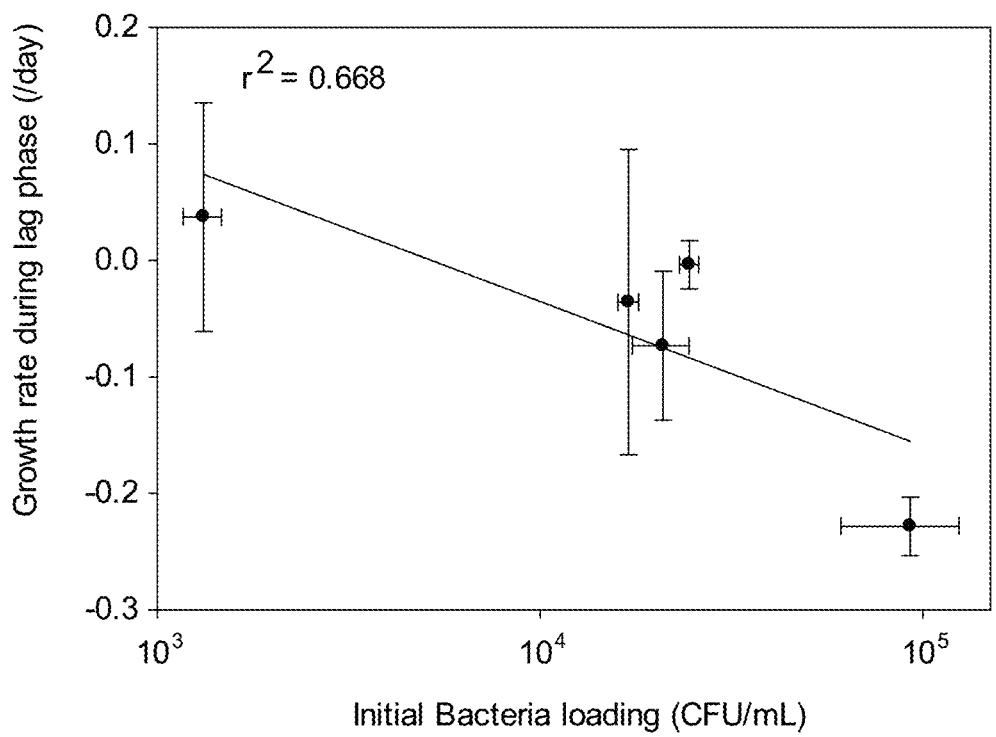

Pretreatment of the ADE with $UV_{254}$ delayed and reduced the duration and extent of the lag phase for all doses. As a direct result, stationary phase was reached 8-10 days sooner for an doses compared with the control group. Further, the lag phase growth rates were linearly correlated to UV dose (FIG. 6). We can attempt to narrow down the potential cause of the diauxic growth in the ADE through eliminating certain aspects. The concentration of dissolved nitrogen (including $NO_3$ species) and phosphorus were monitored throughout the 3 week experiment and were found not to be limiting; all treatments were similar in TDN, $NO_3$, and TDP levels over the course of the experiment including the control group. In addition, TDN and TDP were much higher in the ADE (~3× higher in N) and (~2× higher in P) with levels remaining high throughout the three-week experiment, therefore we can assume that these nutrients are not limiting. Ammonia is potentially inhibitory to phototrophic growth, although concentrations were relatively unchanged in the ADE throughout the duration of our experiments as well as across treatment levels. Other inhibitory components (organic acids) were not measured although these compounds are typically not modified by $UV_{254}$. The absence of an initial lag phase also indicates that inhibitory compounds did not play a role in the algal growth rate [38]. The change in CDOM and absorbance for all UV doses changed optical properties of the wastewater and potentially providing advantages for increased algal growth. Conversely, similar (although less dramatic) changes in the CDOM of PHAE due to $UV_{254}$, with no change in algal growth and no diphasic patterns, were seen. Although this does not completely negate the effect of changes in CDOM, it seems unlikely that growth-related changes could be realized in the ADE and not PHAE.

Figure 5B:
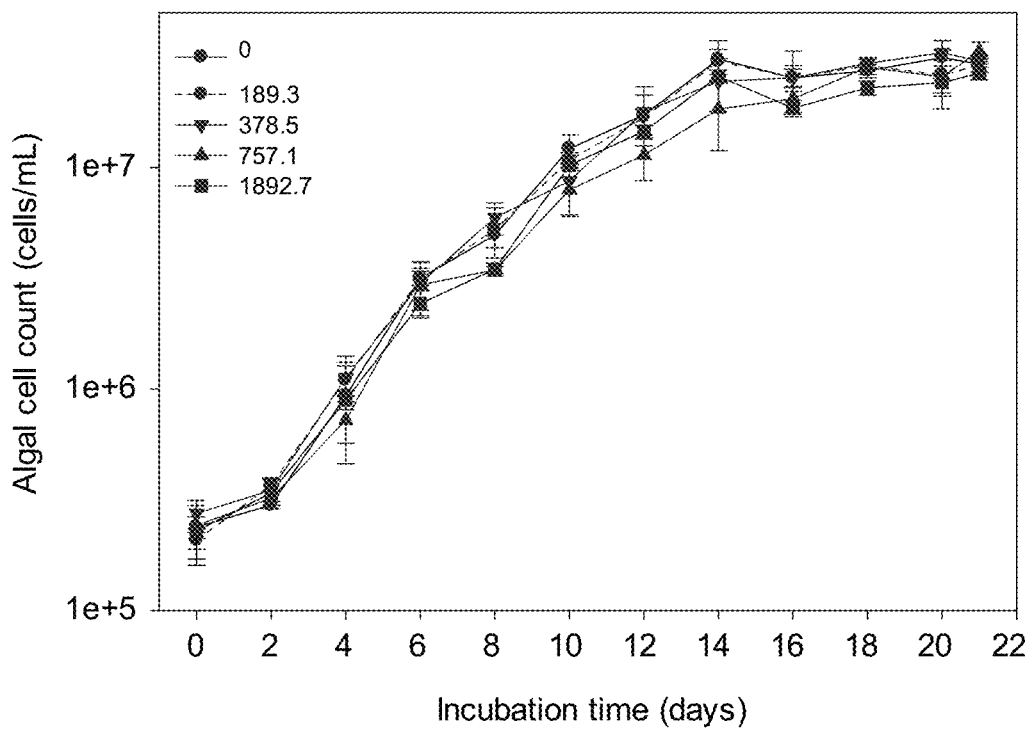

Finally, the presence of an initial indigenous bacteria load (as measured by CFUs) was starkly different for the two different wastewaters as well as across treatment levels. In addition, the initial CFU loading and lag phase growth rate were negatively correlated for the ADE [y=−0.124 x+ 0.462; $r^2$=0.668] (FIG. 5B). Diauxie has previously been seen in algal cultures (*Scenedesmus quadricauda*) grown in sewage treatment effluent where bacteria are abundant, while cultivation in surface waters rarely resulted in dauxic growth [38]. We know that initial presence and subsequent proliferation of bacteria in batch cultures may affect algal growth through multiple pathways: heterotrophic $CO_2$ production, decomposition of organic matter, assimilation of algal by-products, ammonia oxidation, competition for nutrients, and parasitism.

The presence of a biphasic life cycle is also known to exist in marine algae where multiple isomorphic stages may arise in response to environmental pressures such as temperature, light levels, or herbivory, allowing the organism to exploit different ecological niches through adaptation [39]. The separate phases frequently differ in ploidy levels and allow the organism to exist in multiple phases at the same time, differing in their physiology and abundance [39]. Based on our observations, we attribute the dauxic algal growth to the presence of indigenous bacteria that compete for resources with *C. vulgaris*.

Example 3

Pilot Scale Algae Cultivation

Large scale algae cultivation is both technically and economically challenging. Dairy wastewater is identified as an inexpensive nutrient source that can reduce cultivation costs by replacing fertilizers. Unfortunately, multiple inherent physicochemical properties deem dairy wastewater non-ideal for phototrophic growth. Additional challenges are posed in open systems where algae cultures are highly susceptible to invasive species such as competing algae, bacteria, fungus, and rotifers that are inherently present in wastewaters or may be introduced through prolonged cultivation. These invaders can quickly and easily cause culture crash, particularly in large open systems. Ultraviolet (UV) radiation has been shown to modify dairy wastewater, changing dissolved organic matter (DOM), microbial dynamics, and light attenuation to provide an improved phototrophic growth medium in batch cultures. UV pre-treatment has more recently been found to play a key role in enhancing the integrity of pilot scale cultures of *C. vulgaris* cultivated in dairy wastewater. In 100 L semi-continuous open raceways, UV pre-treatment translated to 77% higher cell density of *C. vulgaris* compared to controls after an 8 week steady state period. In addition, total suspended solids (TSS) was elevated in UV cultures (2.58 mg·$L^{-1}$) compared to controls (2.18 mg·$L^{-1}$), increasing harvest yields by 18%. Control cultures were highly susceptible to contamination with filamentous algae compared to UV pre-treated. UV pre-treatment may be useful in large scale open algae systems where invasive species are difficult to control and/or when wastewater is used as the nutrient source.

Methods

Anaerobic Digester Effluent (ADE)

The anaerobic digester effluent (ADE) used for this study were obtained from a mixed plug flow digester (DVO anaerobic digesters) located at Big Sky West Dairy (Good-ing, Id.) and maintained by AgPower Group (Broomfield, Colo.). Before use, the ADE was centrifuged at 10,000 rpm to remove a majority of solids before use. ADE were analyzed for nitrogen, phosphorus, and chemical oxygen demand using methods described herein.

Algal Cultures

*Chlorella vulgaris* (UTEX 2714) was acquired from the University of Texas at Austin Culture Collection (UTEX). *C. vulgaris* was cultured in triplicate in glass dilution bottles and re-cultured on 4 week intervals using Proteose Medium [1] (per liter of filtered water): 0.25 g $NaNO_3$, 0.025 g $CaCl_2.2H_2O$, 0.075 g $MgSO_4.7H_2O$, 0.075 g $K_2HPO_4$, 0.175 g $KH_2PO_4$, 0.025 g NaCl, 1.0 g Proteose peptone, pH adjusted to 6.8.

Before use, *C. vulgaris* was centrifuged for 10 minutes at 12,000 rpm, supernatant was poured off and an equal volume of sterile, filtered water was added to wash the cells and remove any residual media prior to inoculation in ADE. This rinse was performed two times.

Pilot Scale Raceway

Four pilot scale 100 Liter raceways were constructed from HDPE, with 16 cm liquid depth. Submersible pumps were located at each end to promote mixing. Carbon dioxide ($CO_2$) was introduced through an air diffuser and controlled through a solenoid valve and a pH controller (American Marine), with pH set at 6.5. Supplemental light was supplied through Na grow lamps when natural light was low, for a total of 18 hours of light per day.

Ultraviolet Radiation Pre-Treatment of ADE

The UV pre-treatment was performed using a Sterilight compact ultraviolet water purification system, model S1Q-PA equipped with a 14 W UV lamp, emitting $UV_{254}$. The wastewater was pumped through the UV source with a Watson Marlow variable speed pump with 501RL pump head. The pump was equipped with Bioprene tubing (Watson Marlow 903.0064.016), 6.4 mm ID at the inlet (bottom) and outlet (top). Before use and between each treatment, the UV system and tubing were thoroughly cleaned with a 10% bleach solution.

For each UV raceway, 50 L of 5% ADE solution was prepared using ADE and tap water. The 5% ADE solution was passed through the UV light source using a pump speed of 94 rpm (598 mL·$min^{-1}$) for a dose of 378.5 mW·s·$cm^{-2}$. Samples from pre-UV and post-UV were frozen at −20° C. for absorbance scans and nutrient measurements.

Determination of Algal Growth and Biomass Characteristics

Both direct and indirect methods were used to track the progression of algae growth throughout the experiments.

Total Chlorophyll Method:

A methanol solvent extraction method was used as adapted from Hipkins [2]. A 0.5 ml sample of each treatment was centrifuged for 5 minutes at 12,000 rpm to obtain a biomass pellet. The supernatant was removed and disposed of and a 1.0 ml volume of methanol was added to the remaining pellet and sonicated for 10 minutes to break up the pellet, lyse algal cells, and solubilize chlorophyll. Samples were then centrifuged for 5 minutes at 12,000 rpm and the supernatant removed and analyzed by spectrophotometry on an Aquamate spectrophotometer (Thermo Scientific) via absorbance at 650 nm and 665 nm, zeroed with 100% methanol. Chlorophyll content was determined using the following equations [2]: chlorophyll a=(16.5*$A_{665}$)−(8.3*$A_{650}$), chlorophyll b=(33.8*$A_{650}$)−(12.5*$A_{665}$), total chlorophyll=(25.8*$A_{650}$)+(4*$A_{665}$).

Direct Cell Count:

Algal cell density was measured using a hemocytometer counting chamber. A 10 µl sample volume was inserted into the counting chamber and algal cells were counted at 10× magnification. Average cell density was calculated and converting to cells/ml.

Absorbance @ 680 nm:

The direct absorbance (optical density) was measured at 680 nm on an Aquamate spectrophotometer (Thermo Scientific), as an indication of turbidity attributed to combined algal cells, bacteria cells, and dissolved organic matter. The machine was zeroed with deionized water. The $OD_{680}$ is highly dependent on dissolved organic matter (digested manure concentration) and therefore was used as a relative measurement of algal density only.

Total Suspended Solids and Volatile Suspended Solids:

Total suspended solids (TSS) was measured every second day according to EPA method 160.2. Volatile suspended solids (VSS) was measured after combustion at 550° C. for 15 minutes.

Specific Growth Rate:

Exponential growth rates were calculated to include all data points from the end of the lag phase up until the time that stationary phase was reached. To determine the end of the exponential phase a significant change in the rate of change in the day to day direct cell counts was identified, using student t-tests. These changes were used to identify the placement of days associated with exponential and stationary phase growth. A best-fit line employing data points corresponding to the exponential growth phase was then used to determine exponential specific growth rate ($\mu$).

$$\mu = 2.303(\log N_t - \log N_o)/\Delta t \quad \text{Equation 1:}$$

Where:
$\mu$=specific growth rate
$N_o$=cell count at initial time point
$N_t$=cell count at final time point
$\Delta t$=time span used for cell count measurement Lipid Composition:

Freeze dried material (4-5 g) was Soxhlet extracted with CH2Cl2 (150 mL) for at least 16 h and the extractives (lipids) content determined gravimetrically according to ASTM D1108-96.

Carbohydrate:

Carbohydrate analysis was performed using a Phenol-Sulfuric Acid Colorimetric Method (modified Green & Popa, 2010) [3]

Protein:

Biomass protein content was calculated as 6.25 times the elemental nitrogen content as outlined in Food and Agriculture Organization of the United Nations Technical Workshop Report (2003) [5].

Elemental Analysis:

Elemental carbon and nitrogen analysis was performed on a Flash EA 1112 Series Soil Analyzer (Thermo Scientific).

TABLE 3

Pilot scale *Chlorella vulgaris* cultivation in semi-continuous 5% UV pre-treated and untreated (control) 5% ADE wastewater @ 21 day HRT. Dry biomass basis. Mean value (±standard deviation), n = 2.

|  | UV pre-treatment | Control |
|---|---|---|
| First harvest (day 14) | | |
| Total suspended solids (mg/L) | 1.762 (0.084) | 1.202 (0.089) |
| Volatile suspended solids (mg/L) | 1.637 (0.084) | 1.142 (0.074) |
| Lipid (wt/wt %) | 2.97 (0.35) | 2.69 (0.38) |
| Carbohydrate (wt/wt %) | 28.15 (4.22) | 31.03% (1.93) |
| Protein % (wt/wt %) | 38.45 (1.64) | 39.56 (1.64) |
| Elemental carbon (wt/wt %) | 47.79 (0.71) | 48.27 (0.20) |
| Elemental nitrogen (wt/wt %) | 6.15 (0.26) | 6.33 (0.32) |
| Second harvest (day 28) | | |
| Total suspended solids (g/L) | 2.045 (0.112) | 1.530 (0.069) |
| Volatile suspended solids (g/L) | 1.935 (0.114) | 1.470 (0.075) |
| Lipid (wt/wt %) | 3.91 (0.73) | 3.57 (1.00) |
| Carbohydrate (wt/wt %) | 37.47 (2.92) | 34.99 (4.27) |
| Protein (wt/wt %) | 35.02 (1.83) | 38.07 (1.80) |
| Elemental carbon (wt/wt %) | 47.87 (0.56) | 48.12 (0.11) |
| Elemental nitrogen (wt/wt %) | 5.60 (0.29) | 6.09 (0.29) |
| Third harvest (day 42) | | |
| Total suspended solids (g/L) | 2.324 (0.231) | 2.317 (0.120) |
| Volatile suspended solids (g/L) | 2.195 (0.161) | 2.195 (0.113) |
| Lipid (wt/wt %) | 4.28 (1.26) | 1.96 (0.23) |
| Carbohydrate (wt/wt %) | 46.59 (7.39) | 38.60 (4.37) |
| Protein (wt/wt %) | 32.23 (3.86) | 38.72 (1.31) |
| Elemental carbon (wt/wt %) | 47.43 (0.64) | 47.84 (0.06) |
| Elemental nitrogen | 5.16 (0.62) | 6.20 (0.21) |
| Fourth harvest (day 56 day) | | |
| Total suspended solids (g/L) | 2.575 (0.145) | 2.175 (0.056) |
| Volatile suspended solids (g/L) | 2.473 (0.088) | 2.105 (0.053) |
| Lipid (wt/wt %) | 3.56 (0.61) | 2.00 (0.09) |
| Carbohydrate (wt/wt %) | 48.85 (4.26) | 37.21 (3.22) |
| Protein (wt/wt %) | 31.03 (2.45) | 38.85 (1.50) |
| Elemental carbon (wt/wt %) | 48.32 (0.13) | 47.58 (0.15) |
| Elemental nitrogen (wt/wt %) | 4.97 (0.39) | 6.22 (0.24) |

TABLE 4

Projection of costs and profit for pilot scale semi-continuous flow *Chlorella vulgaris* cultivation in 5% UV pre-treated and untreated (control) 5% ADE wastewater @ 21 day HRT. n = 2.

|  | UV pre-treatment | Control |
|---|---|---|
| Dry biomass production (kg/day/acre) | 3.10 | 2.62 |
| Carbon sequestration (kg/day/acre) | 1.50 | 1.25 |
| Nitrogen sequestration (kg/day/acre) | 0.15 | 0.16 |
| UV power consumption ($/day/acre) @$0.08 per kWh | 0.05 | — |
| Profit from sale of biomass as cattle feed ($/day/acre) @$170/ton (DDG) | 0.58 | 0.49 |
| Profit from sale of carbon credits ($/day/acre) @ $6.65/MT | 0.010 | 0.008 |

[1] University of Texas Culture Collection, University of Texas 2013.

[2] Hipkins, M., Photosynthesis energy transduction a practical approach, IRL press, Oxford, Washington D.C. 1986.

[3] Green, T. R., Popa, R., A simple assay for monitoring cellulose in paper-spiked soil. Journal of Polymers and the Environment 2010, 18, 634-637.

[4] Chakraborty, M., McDonald, A. G., Nindo, C., Chen, S., An α-glucan isolated as a co-product of biofuel by hydrothermal liquefaction of *Chlorella sorokiniana* biomass. Algal Research 2013, 2, 230-236.

[5] Maclean, W., Harnly, J., Chen, J., Chevassus-Agnes, S., et al., Food and Agriculture Organization of the United Nations Technical Workshop Report 2003.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention.

The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method of increasing algae production in an agricultural wastewater treatment medium comprising:
    (a) measuring the light absorbance level of agricultural wastewater from at least one wavelength between about 300 nm to about 430 nm prior to treating the agricultural wastewater;
    (b) setting a short wavelength UVc radiation dosage based on the absorbance level;
    (c) treating the agricultural wastewater with short wavelength UVc radiation at a UVc dose of 189.3 mW-s/cm$^2$ to about 757.1 mW-s/cm$^2$ for less than about 300 seconds prior to introduction of algae, thereby generating pre-treated wastewater;
    (d) adding the algae to the pre-treated wastewater and allowing the algae to grow and absorb nutrients present in the pre-treated wastewater, wherein algae growth and production is increased in the pre-treated wastewater in an appropriate absorbance range by as much as 88% over wastewater that is not pretreated by the short wavelength UVc radiation; and
    (e) harvesting the algae or algae bio-material, and recycling the pre-treated wastewater; wherein the agricultural wastewater has at least about 10$^5$ CFU microbes per ml of the wastewater before the treating with the short wavelength UVc radiation.

2. The method of claim 1 wherein the algae is one or more of *Botryococcus braunii*, *Chlorella* sp., *Dunaliella tertiolecta*, *Gracilaria* sp., *Pleurochrysis carterae* (also called CCMP647), and *Sargassum* sp.

3. The method of claim 2 wherein the algae is *Chlorella* sp.

4. The method of claim 1 wherein the UVc does is at a wavelength of less than 280 nm.

5. The method of claim 1 wherein the wastewater light absorbance is from about 2.4 AU or lower.

6. The method of claim 1 wherein the wastewater contains nitrogen, phosphorus, trace minerals, bacteria, and carbon-based products.

7. The method of claim 6 wherein the wastewater is from animal production or contained animal feeding operations (CAFO) sites.

8. The method of claim 1 wherein the wastewater is form dairy production.

9. The method of claim 1 wherein the wastewater is subjected to one or more additional pre-treatments selected from ozone treatment, ultrasound treatment, filtration, hollow fiber filtration, sand filtration, gravel filtration, diatomaceous earth filtration, and activated charcoal filtration.

10. A method of treating agricultural wastewater to enhance algae production comprising:
    measuring the absorbance level from at least one wavelength between about 300 nm to about 430 nm of the wastewater prior to treating;
    setting a short wavelength UVc radiation dosage based on the absorbance level; and
    treating the agricultural wastewater with short wavelength UVc radiation at a dose of about 189.3 mW-s/cm$^2$ to about 757.1 mW-s/cm$^2$ for less than about 300 seconds prior to introduction of algae, wherein the wastewater after treating has changed optical properties that allow for increased light penetration and therefore increased algae growth,
    wherein the agricultural wastewater has at least about 10$^5$ CFU microbes per ml of the wastewater before the treating with the short wavelength UVc radiation.

11. The method of claim 10, further comprising a step of introducing and allowing the algae to grow and absorb nutrients present in the wastewater, wherein algae growth is increased compared to non-pretreated wastewater.

12. The method of claim 10 wherein the changed optical properties include a reduction of light attenuation activity in the range of 280 nm to 320 nm of dissolved organic molecules in the wastewater.

13. The method of claim 10 wherein the treating with the short wavelength UVc radiation results in a decrease in bacterial densities.

14. The method of claim 10 wherein the treating with the short wavelength UVc radiation results in altered chromophoric dissolved organic matter.

15. The method of claim 10 wherein treating the wastewater with the short wavelength UVc radiation is at a wavelength of 254 nm.

16. The method of claim 10 wherein the treating with the short wavelength UVc radiation does not alter an amount of total dissolved phosphorous in the wastewater after treating compared to the wastewater before treating.

* * * * *

UNITED STATES PATENT AND TRADEMARK OFFICE
CERTIFICATE OF CORRECTION

| | | |
|---|---|---|
| PATENT NO. | : 10,920,187 B2 | Page 1 of 1 |
| APPLICATION NO. | : 14/667893 | |
| DATED | : February 16, 2021 | |
| INVENTOR(S) | : Kevin Feris and Maxine Prior | |

It is certified that error appears in the above-identified patent and that said Letters Patent is hereby corrected as shown below:

In the Specification

In Column 1, under Grant Reference Clause, at Lines 17-18:
DELETE: "and grant number DE-AC07-05ID14517"
INSERT: --and number DE-AC07-05ID14517/00041394-00033--

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*